(12) United States Patent
Lewis et al.

(10) Patent No.: US 9,011,923 B2
(45) Date of Patent: Apr. 21, 2015

(54) SUSPENSION FORMULATIONS

(75) Inventors: David Andrew Lewis, Chippenham (GB); Christina Alexandra Keeble, Chippenham (GB); Nicola Kim Whitfield, Ruddington (GB); Tanya Church, Chippenham (GB)

(73) Assignees: Innovata Biomed Limited, Edinburgh (GB); Vectura Limited, Wiltshire (GB)

( * ) Notice: Subject to any disclaimer, the term of this patent is extended or adjusted under 35 U.S.C. 154(b) by 382 days.

(21) Appl. No.: 12/865,142

(22) PCT Filed: Feb. 2, 2009

(86) PCT No.: PCT/GB2009/000261
§ 371 (c)(1),
(2), (4) Date: Apr. 13, 2011

(87) PCT Pub. No.: WO2009/095681
PCT Pub. Date: Aug. 6, 2009

(65) Prior Publication Data
US 2011/0182997 A1    Jul. 28, 2011

(30) Foreign Application Priority Data

Feb. 1, 2008 (GB) .................................. 0801876.4

(51) Int. Cl.
| | |
|---|---|
| *A61K 9/50* | (2006.01) |
| *A61K 9/12* | (2006.01) |
| *A61P 11/08* | (2006.01) |
| *A61P 11/06* | (2006.01) |
| *B29B 9/16* | (2006.01) |
| *A61K 31/00* | (2006.01) |
| *A61K 31/167* | (2006.01) |
| *A61K 31/58* | (2006.01) |
| *A61K 9/00* | (2006.01) |

(52) U.S. Cl.
CPC ................. *A61K 9/50* (2013.01); *A61K 9/0078* (2013.01); *A61K 9/008* (2013.01); *A61K 31/00* (2013.01); *A61K 31/167* (2013.01); *A61K 31/58* (2013.01)

(58) Field of Classification Search
None
See application file for complete search history.

(56) References Cited

U.S. PATENT DOCUMENTS

| | | | |
|---|---|---|---|
| 6,039,932 A | 3/2000 | Govind et al. | |
| 6,153,224 A * | 11/2000 | Staniforth | 424/490 |
| 6,458,338 B1 * | 10/2002 | Adjei et al. | 424/46 |
| 2002/0025299 A1 | 2/2002 | Lewis et al. | |
| 2003/0064031 A1 * | 4/2003 | Humphrey et al. | 424/45 |
| 2003/0114428 A1 | 6/2003 | Sequeira et al. | |
| 2005/0175549 A1 | 8/2005 | Goede et al. | |
| 2008/0026068 A1 * | 1/2008 | Brown et al. | 424/489 |
| 2010/0326437 A1 * | 12/2010 | Zeng | 128/203.15 |
| 2013/0142879 A1 | 6/2013 | Lewis et al. | |

FOREIGN PATENT DOCUMENTS

| | | |
|---|---|---|
| WO | WO 9311745 A1 * | 6/1993 |
| WO | 94/21228 A1 | 9/1994 |
| WO | 96/19198 A1 | 6/1996 |
| WO | 99/38493 A1 | 8/1999 |
| WO | 01/87277 A2 | 11/2001 |
| WO | 02/05784 A1 | 1/2002 |
| WO | 02/43702 A2 | 6/2002 |
| WO | WO 0243702 A2 * | 6/2002 |
| WO | 2005/025540 A2 | 3/2005 |
| WO | 2005/077339 A1 | 8/2005 |
| WO | 2006/059152 A2 | 6/2006 |
| WO | WO 2008013938 A2 * | 1/2008 |
| WO | 2008/152398 A2 | 12/2008 |

OTHER PUBLICATIONS

PCT International Search Report for PCT/GB2009/000261, filed Feb. 2, 2009.
Non-Final Office Action for continuation application U.S. Appl. No. 13/752,480 (mailed Aug. 20, 2014).

* cited by examiner

*Primary Examiner* — Frederick Krass
*Assistant Examiner* — Michael P Cohen
(74) *Attorney, Agent, or Firm* — LeClairRyan, a Professional Corporation

(57) ABSTRACT

The present invention relates to suspension formulations, especially those for delivering a pharmaceutically active agent in aerosol form using a spray or aerosol device, such as a pressurized metered dose inhaler (pMDI). The formulations may be for pulmonary, nasal, buccal or topical administration, but are preferably for pulmonary inhalation.

17 Claims, No Drawings

SUSPENSION FORMULATIONS

This is a national stage application under 35 U.S.C. §371 of PCT/GB2009/000261, filed Feb. 2, 2009, which claims priority to GB 0801876.4, filed Feb. 1, 2008.

This is a national stage application under 35 U.S.C. §371 of PCT/GB2009/000261, filed Feb. 2, 2009, which claims priority to GB 0801876.4, filed Feb. 1, 2008.

The present invention relates to suspension formulations, especially those for delivering a pharmaceutically active agent in aerosol form using a spray or aerosol device, such as a pressurised metered dose inhaler (pMDI). The formulations may be for pulmonary, nasal, buccal or topical administration, but are preferably for pulmonary inhalation.

BACKGROUND TO THE INVENTION

Since the pMDI was introduced in the mid 1950s, inhalation has become the most widely used route for delivering bronchodilator drugs and steroids to the airways of asthmatic patients. Compared with oral administration of bronchodilators, inhalation offers a rapid onset of action and a low instance of systemic side effects. More recently, inhalation from a pressurized inhaler has been a route selected for the administration of other drugs.

The pMDI is dependent upon the propulsive force of a propellant system used in its manufacture to dispense the drug formulation from the device in a form that may be inhaled by a patient. The propellant generally comprises a mixture of liquefied hydrofluorocarbons (HFAs) which are selected to provide the desired vapour pressure and stability of the formulation. Propellants HFA 227 (1,1,1,2,3,3,3-heptafluoropropane) and HFA 134a (1,1,1,2-tetrafluoroethane) are the currently the most widely used propellants in aerosol formulations for inhalation administration.

It has been suggested that hydrocarbons, such as n-butane, isobutanol, and propane be considered as CFC replacements in aerosol formulations. However, it has been found that such hydrocarbons have low densities relative to the pharmaceutically active agents included in the formulations. Where suspension formulations are prepared using such propellants, the formulations sediment rapidly and are unacceptable. Furthermore, the solubility of many drugs in these hydrocarbons is poor, which means that it is difficult to prepare formulations that are solutions which contain suitable amounts of drug.

The formulations currently dispensed using pMDIs generally comprise a pharmaceutically active agent, one or more propellants, and optionally excipients and adjuvants such as co-solvents, (conventional) surfactants, flavouring agents and lubricants.

The excipients should be miscible with the propellants in the amounts employed. Suitable excipients include alcohols such as ethyl alcohol, isopropyl alcohol, propylene glycol, hydrocarbons such as propane, butane, isobutane, pentane, isopentane, neopentane, and other propellants much as those commonly referred to as propellants 11, L2, 114, 113, 142b, 152a 124, and dimethyl ether.

Preferred adjuvants are liquids or gases at room temperature and at atmospheric pressure. The combination of one or more of such adjuvants with a propellant such as HFA 134a or HFA 227 provides a propellant system which has comparable properties to those of propellant systems based on CFCs of the past decades, allowing use of known surfactants and additives in the pharmaceutical formulations. This is particularly advantageous since the safety and use of such compounds in metered dose inhalers for drug delivery to the human lung is well established. Additives that are well know include ethanol, water, glycerol and polyethylene glycol.

The pharmaceutically active agents present in formulations used in pMDIs and similar propellant-driven devices are either dissolved or suspended in a liquefied propellant gas. Most pharmaceutically active agents are not sufficiently soluble in pure propellants, either HFAs or CFCs, for simple two component formulations of active agent and propellant to be practical. Although, through the incorporation of a co-solvent such as ethanol, many active agents can be dissolved in the resulting formulation, formulations in which the active agent, in a micronised or particulate form, is suspended in the propellant are generally preferred and more common. There are several reasons for this. It is important to control the size of the particles or droplets in the aerosol spray produced by a pMDI, or like device. For example, if the particles or droplets are to penetrate deep into the lungs, they should have a mass median aerodynamic diameter (MMAD) of less than 10 µm. Conversely, if the spray is for buccal or nasal delivery, the particles or droplets must have an MMAD of significantly greater than 10 µm, in order to prevent them from entering the lungs. Controlling the size of the particles in an aerosol spray produced from a purely liquid formulation is more difficult than it is with a formulation comprising a suspended solid particulate pharmaceutically active agent. In the former case, many environmentally influenced factors, such as solvent evaporation rates, will have an effect on particle size, whereas the size of the particles produced by a suspension formulation is determined largely by the size of the active agent particles employed in its preparation, and this is a parameter that can be effectively controlled.

A second, but important, reason for suspension formulations being preferred is that many pharmaceutically active agents are chemically more stable as solids than they are when in solution. For example, most pharmaceutically active compounds are much more susceptible to degradation by acid or alkali when in solution than they are when solid. It is also simply impossible to render many pharmaceutically active agents sufficiently soluble in a pharmaceutically acceptable propellant system, for a solution formulation to be a realistic option for them.

A further, reason for suspension formulations being preferred to solutions is that solution formulations may be restricted by the drug loading capacity of the solvent. Drug loading levels will vary depending on the solvent and solute used, however, suspension systems are not limited in this way and routinely allow higher drug loads to be incorporated into the formulations.

Dissolving an active agent to form a solution negates the need to micronise the drug to obtain a suitable particle size. However, not all active agents are stable when in solution or in direct contact with the excipients and propellant.

Previous disclosure, for example by 3M, has demonstrated that the solubility of many drugs may be enhanced in the presence of ethanol. However, high levels of ethanol may impart a negative effect on a suspension system by dissolving the drug.

Dispersing agents, such as surfactants, are commonly employed in suspension aerosol formulations in order to ensure that the particles of pharmaceutically active agent can be dispersed within the propellant system without an undue degree of agitation and remain so dispersed for a sufficiently long period of time for the effective operation of the pMDI to be ensured. Surfactants can also provide useful lubrication to the metering valve's mechanism. However, one of the problems which has arisen in the development of HFA-based suspension formulations for use in pMDI and like devices, is that many of the surfactants commonly employed as dispersing agents in CFC-based formulations are substantially insoluble in HFA 134a and HFA 227 and, thus, are substantially ineffective in simple formulations based on these latter two propellants, or other HFA propellants.

One solution to this problem, which was proposed in EP 0 372 777, is to incorporate a co-solvent, such as ethanol, having a greater polarity than the HFA propellant in the formulation, in order to dissolve the surfactant or other dispersing agent. Whilst the presence of such a co-solvent allows most dispersing agents to be dissolved in HFA based formulations, it will also cause certain pharmaceutically active agents to dissolve, at least partially, in the co-solvent/propellant system. This phenomenon is especially disadvantageous in formulations for delivery into the lungs because, over time, it causes the particles of active agent in the formulation to grow, possibly to a size in excess of that generally considered to be acceptable for inhalation, i.e., to have a MMAD of greater than 10 μm. Further disadvantages associated with the use of ethanol as a co-solvent include its potential toxicity, its capacity to increase a formulation's propensity to absorb water and the fact that many patients dislike the taste that its presence can impart to a formulation.

Another method for incorporating a surfactant or dispersing agent which has been previously proposed is to coat the particles of pharmaceutically active agent with the surfactant or dispersing agent before they are mixed with the propellant and to suspend the coated particles in the HFA propellant without using any co-solvent.

One process which has been proposed in order to achieve such coating involves the steps of dissolving the surfactant in a solvent in which the pharmaceutically active agent is substantially insoluble, mixing a quantity of the pharmaceutically active agent, in micronised form, into the surfactant solution and isolating particles of surfactant coated active agent either by filtration and drying, or by removal of the solvent by evaporation. Although the literature suggests (see WO 92/08447 and WO 91/04011) that formulations prepared in this manner are effective, in the sense that they allow stable dispersions of powdered active agent to be formed in the HFA propellant, it has so far not proven possible, in practice, to manufacture useful formulations in this way. For example, it is difficult to achieve a uniform coating using techniques of this nature because the manner in which the dispersing agent precipitates from the evaporating solvent can be unpredictable.

WO 2006/059152 proposes coating the particles of pharmaceutically active agent with a dispersing agent by fusing solid, particulate dispersing agent to the surfaces of the active particles by mechanical means, such as a milling step. The resulting composite or hybrid particles are readily dispersible within HFA propellant systems.

A further technique which has been proposed is to suspend a powdered mixture consisting of particles of a calcium, magnesium or zinc salt of palmitic or stearic acid and particles of pharmaceutically active agent in the propellant.

A further problem that is often associated with known formulations for delivery using devices such as pMDIs is their stability and consequently their shelf life. This especially applies to ethanol-free suspension formulations. These formulations and the pMDI products have a reduced shelf life due to moisture ingress. Generally, when the formulations are prepared they are free of moisture. However, once opened from their foil packaging, the shelf life of the pMDI formulation is dramatically reduced due to the ingress of moisture. The ingress of moisture can change the suspension characteristics, often leading to increased flocculation rate which leads to poor product performance and poor drug delivery.

It is an aim of the present invention to provide improved suspension formulations comprising a pharmaceutically active agent for delivery using a spray or aerosol device, such as a pressurised metered dose inhaler (pMDI).

In particular, it is desirable for the active agent within the suspension formulations to be stable, so that the physical and chemical state of the active agent is retained when the formulation is made and over time as it is stored and used. More specifically, it is an aim of the present invention to provide suspension formulations that allow the delivery of an active agent in amorphous form (and therefore exhibiting preferable dissolution characteristics).

It is also an aim of the present invention to provide a suspension formulation in which the suspension itself is physically stable, in that it exhibits a reduced tendency to flocculate and/or for the suspended particles to sediment. It is also an aim of the present invention to provide suspension formulations with a long shelf-life and, in particular, formulations that are not sensitive to moisture ingress.

SUMMARY OF THE INVENTION

In a first aspect of the present invention, a composition is provided which is suitable for delivery using a pressurised metered dose inhaler, the composition comprising a suspension of a pharmaceutically active agent in one or more propellants, wherein composition further comprises one or more suspension stabilisers to maintain the physical state of the active agent in the composition, said suspension stabilizer may be insoluable.

In a preferred embodiment of the invention, the composition comprises the pharmaceutically active agent in amorphous form and the suspension stabilisers serve to maintain that amorphous form in the suspension.

Preferred suspension stabilisers include amino acids and saccharides. Preferred amino acids include aspartame, leucine, isoleucine, lysine, valine, methionine, cysteine, and phenylalanine. Leucine is especially preferred. Preferred saccharides include disaccharides such as trehalose.

An alternative suspension stabiliser is a vinyl polymer such as polyvinylpyrrolidone (PVP).

In one embodiment of the invention, the compositions comprise two or more active agents and these are preferably compatible with one another. The active agents may be included as separate particles in the suspension. Alternatively, a particle in the suspension may comprise more than one active agent.

In a preferred embodiment of the present invention, the active agent is included in the composition as coated particles. The coating or encasement surrounding the particles preferably stabilises the active agent, ensuring that it maintains its physical state. Preferred coatings comprise suspension stabilisers such as saccharides and amino acids, as discussed above. The coated particles of active agent may be in the form of microcapsules, microspheres, or microsponges. The coating materials may be trehalose and/or leucine. In some embodiments, the coating may further include at least one other amino acid. The compositions and/or the coated particles may also include a surfactant. In some preferred embodiments, the coated active particles are formed by spray drying.

There are a number of reasons why a particulate active substance might need to be formulated within a protective encasement. For example, the active may be physically or chemically unstable, or incompatible with another substance with which it needs to be formulated. It may need protection against, for example, moisture, light, oxygen or other incompatible chemicals. The surface coating may alternatively be required to delay release of the active for a desired time period or until it reaches an appropriate site, or to target its delivery to such a site. The surface coating may alternatively be required to minimise interparticle and or particle device interaction.

In a preferred embodiment, the coating of encasement is complete or substantially complete, so that the active agent is completely surrounded by the coating material. In other embodiments, the coating may be partial, in which case the coating preferably covers at least 40%, at least 50%, at least 60%, at least 70%, at least 80%, at least 90% or at least 95% of the surface of the active particle.

Pharmaceutical formulations, including those to be dispensed using a pMDI, containing one or more drugs are known in the art. These multi-active formulations require the solubility characteristics of the actives to be complementary in order for this to be achieved for example solution and suspension, suspension and suspension or solution and solution. The term active refer to one or more drugs, prodrugs, salts or esters thereof as outlined below.

It has been found that drugs which are at least slightly soluble in hydrocarbon propellants will exhibit an enhanced solubility in the propellant in the presence of high levels of a co-solvent such as ethanol.

In the context of the present invention, an active agent is said to be "insoluble" or "substantially insoluble" in the formulation if it has a solubility in the formulation of less than 25 g/L. "Insoluble" active agents may also have a solubility of less than 20 or less than 15 g/L. Where an active agent is said to be "poorly soluble" or "slightly soluble" in the formulation, the active has a solubility in the formulation of less than 50 g/L or less than 40 g/L. Preferably, the solubility of an active agent in the formulation is measured at ambient temperature (20° C.) and at atmospheric pressure.

Historically, ethanol was added to the pMDI formulation to dissolve surfactants and valve lubricants. It has since been found that the ethanol is also capable of dissolving the drug within the pMDI formulation.

Surprisingly it has now been found that including co-solvents such as ethanol in small amounts can be highly beneficial. More specifically, it is desirable to include in the suspension formulations of the present invention a co-solvent in an amount which does not cause total dissolution of the active agent. At such low concentrations, the co-solvent has a beneficial effect on the suspension system, without destroying the suspension and forming a solution. The co-solvent has been found to reduce flocculation and sedimentation.

According to a second aspect of the present invention, a composition is provided which is suitable for delivery using a pressurised metered dose inhaler, the composition comprising a suspension of a pharmaceutically active agent in one or more propellants, wherein composition further comprises a co-solvent in an amount which has little effect on the solubility of the active agent and which does not cause significant dissolution of the active agent in the composition.

Suitable co-solvents include, but are not limited to, alcohols such as ethanol, methanol, ethers, and polyethylene glycol.

A preferred co-solvent is ethanol and it is preferably included in the formulations of the present invention in an amount below 1% w/w. At this concentration, the ethanol tends to have little effect on the solubility of an active agent and this small amount of ethanol does not cause complete or significant dissolution of the active agent in the formulation used.

With this information the skilled artisan would know that the various components of the compositions according to the invention would need to be altered slightly to account for the inherent solubility of the active agent in the formulation.

The inclusion of between 0.1 and 0.5% w/w ethanol in the compositions of the present invention is particularly advantageous because this enhanced suspension has been shown to permit the active agent to retain its physical state in the composition, preferably remaining in the amorphous state and not reverting to the crystalline state. In other words, there is enough ethanol in the composition to assist in the maintenance of the suspension, extending the duration of particle suspension and minimising flocculation.

A particular advantage associated with the inclusion of small amounts of co-solvent in the suspension compositions of the invention is that this allows the compositions to be prepared so that they include a level of moisture from the beginning of the formulation procedure. This means that the suspension is not unduly affected by moisture ingress when the product is first used and removed from any protective packaging, as is observed with some known suspension formulations, as discussed above. Desiccation processes during the preparation of the compositions according to the present invention are not required when the co-solvent is present. What is more, the addition of these low levels of co-solvents, such as ethanol, provide further composition flexibility to the final formulation by permitting the addition of water, acids and surfactants if so required. The addition of these additives is not recommended and may be detrimental to desiccated systems.

In a preferred embodiment of the present invention, the suspension is prepared using spray dried materials. Spray drying active agents in conjunction with a suspension stabiliser such as leucine or derivatives thereof and/or trehalose results in an unexpected level of protection of the amorphous drug state, thereby further preventing reversion to the crystalline form. Furthermore this arrangement confers an enhanced suspension characteristics within propellant vehicles (such as HFA 134a and/or HFA 227) with or without the addition of a co-solvent, thereby extending the duration of particle suspension and minimising flocculation.

It has surprisingly been found that by the appropriate selection and addition of a co-solvent, such as ethanol, to the formulation a number of advantages are available to the final system. These include suppression of propellant flashing at the spray orifice thereby preventing drug deposition directly over the spray orifice and thus reducing potential orifice blockage. Surprisingly, low levels of ethanol, for example 0.1% w/w, have been found to improve the consistency of the valve metering. In addition to this benefit, low levels of co-solvents such as ethanol allow dissolving of valve lubricants, surfactants and/or excipients such as oleic acid, propylene glycol which may also act as formulation excipients and/or stabilisers. However, to ensure the physical state of the drug is not altered during suspension within the pMDI, the selection of the co-solvent content must not result in a significant increase in solubility of the active or additive within the system.

Table 1 below reports the solubility of some typical drugs used within inhalation products for treating respiratory diseases. The data in Table 1 demonstrates that ethanol addition can increase the solubility of drugs within HFA systems. However, it has been surprisingly found that the addition of ethanol to HFA 227 systems does not result in solubilisation of actives above that determined for pure HFA 134a. It therefore follows that HFA 227 with small additions of ethanol not only results in drug solubility levels below that of HFA 134a systems but also results in the aforementioned advantages of ethanol addition to the propellant based systems. Therefore, in a preferred embodiment of the present invention, the composition will comprise the propellant HFA 227 and will contain quantities of ethanol that result in drug solubility below 1 µg per 50 µl, or more preferably below 0.1 µg per 50 µl, or more preferably below 0.05 µg per 50 µl.

In some embodiments of the first aspect of the present invention, the suspension composition comprising the suspension stabiliser further comprises a co-solvent in an amount which has little effect on the solubility of the active agent and which does not cause significant dissolution of the active agent in the composition.

In some embodiments of the second aspect of the present invention, the suspension composition comprising the co-solvent further comprises one or more suspension stabilisers.

It is important that the suspension stabilisers used in the present invention do not dissolve within the composition and, in particular, in the propellant system used. Trehalose has been determined to be insoluble (observed to be <0.12 µg/50 µl) in HFA 134a or HFA 227 with up to 12% w/w ethanol and only slightly soluble in 30% w/w ethanol (3.3 µg/50 µl in HFA 134a, 2.7 µg/50 µl in HFA 227). Addition of 0.5% w/w propylene glycol or 0.01% w/w oleic acid did not increase trehalose solubility (<0.12 µg/50 µA in either 3% w/w ethanol when manufactured with either HFA 134a or HFA 227. The addition of 1.2% w/w water was not found to increase trehalose solubility (<0.12 µg/50 µl) in 12% w/w ethanol formulation manufactured with either HFA 134a or HFA 227.

Leucine has been determined to be insoluble (observed to be <0.08 µg/50 µl) in HFA 134a or HFA 227 with up to 30% w/w ethanol. Addition of 0.5% w/w propylene glycol or 0.01% w/w oleic acid did not increase leucine solubility (<0.08 µg/50 µl) in 3% w/w ethanol when manufactured with either HFA 134a or HFA 227. The addition of 1.2% w/w water was not found to increase leucine solubility (<0.08 µg/50 µl) in 12% w/w ethanol formulation manufactured with either HFA 134a or HFA 227.

TABLE 1

Solubility of drugs within HFA 134a, represented as µg per 50 µl

| Drug | EtOH addition (% w/w) | | | | |
| --- | --- | --- | --- | --- | --- |
| | 0 | 1 | 5 | 12 | 20 |
| Fluticasone Propionate | 0.48 | 1.45 | 9.41 | 48.80 | 86.60 |
| Ipratropium Bromide | 0.03 | 0.24 | 3.50 | | |
| Tiotropium Bromide | 0.00 | 0.01 | 0.33 | | |
| Budesonide | 1.43 | 4.38 | 35.41 | | |
| Formoterol | 0.00 | 0.03 | 0.73 | | |

TABLE 2

Solubility of drugs within HFA 227, represented as µg per 50 µl

| Drug | EtOH addition (% w/w) | | | |
| --- | --- | --- | --- | --- |
| | 0 | 0.2 | 1 | 5 |
| Fluticasone Propionate | 0.22 | 0.23 | 0.83 | 4.78 |
| Ipratropium Bromide | 0.00 | — | 0.04 | 4.32 |
| Tiotropium Bromide | 0.00 | — | 0.00 | 0.07 |
| Budesonide | 1.66 | — | 5.61 | 45.16 |
| Formoterol | 0.00 | — | 0.02 | 0.23 |

There are few drugs which are soluble at therapeutic dosage levels in aerosol propellants alone, and one example is estradiol dipropinoate. Solution formulations comprising other, less soluble active agents have been prepared using a toxicity approved polar co-solvent, such as ethanol.

A particularly preferred formulation according to the invention comprises particles comprising an active agent formulated with leucine and optionally trehalose, for delivery to a patient, wherein the particle remains substantially unaltered in a pMDI formulation.

The skilled artisan would be able to determine the precise drug loading for formulations according to the present invention. As an example, the following compounds and their proposed concentrations are disclosed, for reference.

Tiotropium bromide constitutes from about 0.001% (~0.4 µg per dose in 100 µl valve) to 0.16% by weight (~200 µg per dose in 25 µl valve), preferably from about 0.010 to about 0.400% by weight, more preferably about 0.0150 to about 0.300% by weight, and most preferably about 0.0300 to about 0.200% by weight of the formulation.

Ipratropium bromide constitutes from about 0.001% (~0.4 µg per dose in 100 µl valve) to 0.16% (~200 µg per dose in 25 µl valve), preferably from about 0.010 to about 0.400%, more preferably about 0.0150 to about 0.300%, and most preferably about 0.0300 to about 0.200% by weight of the formulation.

Salbutamol sulphate constitutes from about 0.01% (~3 µg per dose in 100 µl valve) to 0.98% (~1200 µg per dose in 25 µl valve), preferably from about 0.025 to about 0.6%, more preferably about 0.050 to about 0.5%, and most preferably about 0.075 to about 0.4% by weight of the formulation.

Salbutamol constitutes from about 0.03% (~10 µg per dose in 100 µl valve) to 0.8% (~1000 µg per dose in 25 µl valve), preferably from about 0.04 to about 0.7%, more preferably about 0.05 to about 0.5, and most preferably about 0.06 to about 0.35% by weight of the formulation.

Formoterol fumarate constitutes from about 0.002% (~0.6 µg per dose in 100 µl valve) to 0.12% (~150 µg per dose in 25 µl valve), preferably from about 0.025 to about 0.06%, more preferably about 0.050 to about 0.03%, and most preferably about 0.075 to about 0.02% by weight of the formulation.

Fluticasone propionate constitutes from about 0.02% (~5 µg per dose in 100 µl valve) to 2% (~2500 µg per dose in 25 µl valve), preferably from about 0.018 to about 1%, more preferably about 0.012 to about 0.5%, and most preferably about 0.010 to about 0.25% by weight of the formulation.

Salbutamol xinafoate constitutes from about 0.014% (~5 µg per dose in 100 µl valve) to 2% (~2500 µg per dose in 25 µl valve), preferably from about 0.016 to about 0.5%, more preferably about 0.018 to about 0.1%, and most preferably about 0.020 to about 0.06% by weight of the formulation.

The skilled artisan will be able to calculate the appropriate drug loading based upon the values of one propellant and relate HFA 227 (density 1.415 g/ml) to HFA 134a (density 1.216 g/ml) and vice versa. This approach assumes that the drug density falls between that of HFA 227 (density 1.415 g/ml) to HFA 134a (density 1.216 g/ml). The creation of a suspension formulation may be achieved by initially using a single propellant to suspend the drug particles. Initial attempts will most likely result in the drug density falling either above or below the propellant density. This may be rectified with the incremental addition of the second propellant to the first, which will result in a combined "titrated" propellant with a density which has been tailored to match the density of the drug thereby creating a suspension.

The skilled artisan would be able to determine the appropriate amounts of suspension stabilisers to be included in formulations according to the present invention. As an example, the following compounds and their proposed concentrations are disclosed, for reference.

Leucine may be included in the compositions according to the present invention in an amount of from about 0.00003% to 2%, preferably from about 0.0001 to about 1%, more preferably about 0.0002 to about 0.2%, and most preferably about 0.0003 to about 0.02% by weight of the formulation.

Trehalose may be included in the compositions according to the present invention in an amount of from about 0.00003% to 2%, preferably from about 0.0001 to about 1%, more preferably about 0.0002 to about 0.2%, and most preferably about 0.0003 to about 0.02% by weight of the formulation.

Ethanol may be included in the compositions according to the present invention in an amount of from about 0.0010 to about 2% by weight of the total formulation, preferably about 0.0025 to about 0.5% by weight, preferably about 0.0050 to about 0.2% by weight and most preferably about 0.01 to 0.15% by weight of the aerosol formulation.

Oleic acid may be included in the compositions according to the present invention in an amount of from about 0.0001% to about 1% by weight, preferably from about 0.0025 to about 0.5% by weight preferably from about 0.0050 to about 0.1% by weight, more preferably about 0.0075 to about 0.1 by weight, and most preferably about 0.01 to 0.02% by weight of the aerosol formulation.

Glycerol may be included in the compositions according to the present invention in an amount of from about 0.0001% to about 5% by weight, preferably from about 0.0025 to about 4% by weight, more preferably about 0.005 to about 3% by weight, more preferably about 0.0075 to about 2.5% by weight, and most preferably about 0.01 to 1.0% by weight of the aerosol formulation.

Propylene glycol may be included in the compositions according to the present invention in an amount of from about 0.0001% to about 5% by weight, preferably from about 0.0025 to about 4% by weight, more preferably about 0.005 to about 3% by weight, more preferably about 0.0075 to about 2% by weight, and most preferably about 0.01 to 1.0% by weight of the aerosol formulation.

Polyvinylpyrrolidone may be included in the compositions according to the present invention in an amount of from about 0.0001% to about 5% by weight, preferably from about 0.0025 to about 4% by weight, more preferably about 0.005 to about 3% by weight, more preferably about 0.0075 to about 2.5% by weight, and most preferably about 0.01 to 1.0% by weight of the aerosol formulation.

In one embodiment of the present invention, the aerosol formulations do not contain a propellant other than HFA 227. Most preferably, the aerosol formulations of the present invention do not contain ingredients other than the propellant, ethanol, or the excipients mentioned above.

Preferred compositions according to this invention exhibit substantially no change in the amorphous or crystalline state of the drug over a prolonged period. Preferably the prolonged period is at least 1 year, more preferably at least 2 years, and even more preferably at least 3 years and most preferably at least 4 years. The formulations disclosed herein remain substantially and readily redispersible and, upon redispersion, do not flocculate quickly, thereby ensuring reproducible drug dosing.

The term "flocculate" in the context of the present application is generally used to describe the process whereby formulation components or particles assemble into floccules or flocculent aggregates imparting a typically granular appearance to the suspension.

The term suspension in the context of the present application is generally used to describe a mixture in which particles are uniformly suspended within a fluid. The suspension often possesses a typically milky appearance for a period of time.

When present in the compositions of the present invention as an additive material, amino acids have been found to provide a high respirable fraction of the active material and good flow properties of the powder. The additive material may comprise one or more of any of the following amino acids: aspartame, leucine, isoleucine, lysine, valine, methionine, cysteine, and phenylalanine. A preferred amino acid is leucine, in particular L-leucine, di-leucine and tri-leucine. Although the L-form of the amino acids is generally preferred, the D- and DL-forms may also be used. Additive materials may also include, for example, metal stearates such as magnesium stearate, phospholipids, lecithin, colloidal silicon dioxide and sodium stearyl fumarate, and are described more fully in WO 96/23485, which is hereby incorporated by reference.

In one embodiment of the present invention, the composition comprises active particles comprising additive, at least 50%, at least 70% or at least 90% of the particles having a Mass Median Aerodynamic Diameter (MMAD) of no more than about 10 μm. In another embodiment, at least 50%, at least 70% or at least 90% of the active particles have an MMAD of from about 1 μm to about 5 μm. In yet another embodiment, at least 50%, at least 70% or at least 90% of the active particles have aerodynamic diameters in the range of about 0.05 μm to about 3 μm.

Microparticles refer to substantially spherical particles having a mean diameter within about 0.020 μm to 1000 μm and includes microcapsules, microspheres, and microsponges.

As used herein, the term "microcapsule" refers to a particle wherein a wall, shell or coating encases a core. In some embodiments, the core comprises the active agent. As used herein, the term "microsphere" refers to a microparticle wherein an active agent is embedded within a solid matrix. As used herein, the term "microsponge" refers to a microparticle wherein an active agent is embedded within a polymeric matrix comprising an open-cell structure.

According to a particular embodiment of the present invention, there is provided an aerosol formulation which contains a dispersed phase, comprising a propellant selected from HFA 134a or HFA 227 and mixtures thereof; a co-solvent; suspension stabilizers and a pharmaceutically active agent, in which the active agent is in the composition in a manner which permits the preservation of its physical form.

The term suspension aerosol means that the active agent is in particulate form and is substantially insoluble in other components of the composition.

All weight percentages recited herein are based on the total weight of the formulation unless otherwise indicated.

The compositions according to the present invention, and in particular those including a co-solvent in the small amounts discussed, have the further advantage that they can provide improved valve metering performance. Conventional valves for use in devices such as pMDIs tend to be specifically designed for either an ethanol-containing solution formulation, or an ethanol-free suspension. The compositions according to the present invention can be dispensed using either type of valve and the nature of the compositions means that they provide the composition flexibility to allow them to be formulated to improve valve performance.

As used herein, the term "Nominal Dose" is the amount of drug metered in the metering chamber, also known as the Metered Dose (MD). This is different to the amount of drug that is delivered to the patient which is referred to a Delivered Dose. The Delivered Dose, also referred to as the Emitted Dose, (ED) refers to the dose that leaves the device and it is measured as set out in the current European Pharmacopoeia monograph for inhalation products. The therapeutic dose is the dose range that is proven to be clinically effective.

As used herein, the term "fine particle fraction" (FPF) is normally defined as the FPD (the dose that is <5 μm) divided by the Delivered Dose (ED) which is the dose that leaves the device. The FPF is expressed as a percentage. Herein, the FPF of ED is referred to as FPF (ED) and is calculated as FPF (ED)=(FPD/ED)×100%.

The fine particle fraction (FPF) may also be defined as the FPD divided by the Metered Dose (MD) which is the dose in the blister or capsule, and expressed as a percentage. Herein, the FPF of MD is referred to as FPF (MD), and is calculated as FPF (MD)=(FPD/MD)×100%.

The term "ultrafine particle fraction" (UFPD) is used herein to mean the percentage of the total amount of active material delivered by a device which has a diameter of not more than 3 μm. The term percent ultrafine particle dose (% UFPD) is used herein to mean the percentage of the total metered dose which is delivered with a diameter of not more than 3 (i.e., % UFPD=100*UFPD/total metered dose). "Actuation of a pMDI inhaler" refers to the process during which a dose is discharged from the metering chamber.

Preparing pMDI Formulations

The spray drying of material for subsequent incorporation into a pMDI surprisingly maintains the structural state prior to and during atomisation. Traditionally used for dry powders, spray drying is not the most efficient method of particle manufacture due to the low powder recoveries. Amorphous material that has been formulated as a dry powder often results in an unstable formulation.

The suspension aerosol formulation of this embodiment may be prepared by first preparing a solution of an active agent with a suspension stabiliser, such as leucine and optionally trehalose, and spray drying the solution at conditions known to those skilled in the art. The resulting powder may then be added to a propellant. The propellant may be present in a solution comprising a co-solvent, such as ethanol. The amount of co-solvent present is preferably not enough to dissolve the spray dried particles when they are added. In the case of ethanol, it is preferably included in an amount that means that the ethanol makes up less than 1% w/w based upon the final composition. The propellant is preferably HFA 227. The particles in the suspension comprise the pharmaceutically active agent.

In order to produce a pMDI comprising the composition, the spray dried particles comprising the active agent are placed in a separate aerosol vial, a metered valve is crimped onto the vial and the vial is pressure filled with the previously prepared propellant/excipient solution. The particles are then dispersed in the solution by mixing or homogenizing. The addition of the propellant/excipient solution minimises the likelihood of the active being dissolved by the excipient, thereby retaining particle integrity. The propellant dilutes the excipients further minimizing undesirable excipient-active interaction. The final level of excipient may need to be adjusted to minimise dissolution of active in the excipient. This technical challenge may be avoided when the active is not soluble in the excipient alone or in the propellant/excipient solution.

Alternatively, the formulations can be prepared by first placing the spray dried particles, the co-solvent and excipients mentioned above in an aerosol vial. In order to prepare a formulation in this manner, a continuous valve is crimped onto the vial and the vial is then pressure filled with propellant and shaken to disperse the active.

Certain composition according to the invention require the inclusion of conventional surface active agents, to provide the compositions with the conventional properties and benefits that such agents are known to afford. For example, aside from the ability to conserve the internal state of the particles, the surface active agents minimise interparticle adherence thereby minimising agglomerate formation.

Drug List

The present invention can be carried out with any pharmaceutically active agent. Specific active agents or drugs that may be used include, but are not limited to, agents of one or more of the following classes listed below.

1) Adrenergic agonists such as, for example, amphetamine, apraclonidine, bitolterol, clonidine, colterol, dobutamine, dopamine, ephedrine, epinephrine, ethylnorepinephrine, fenoterol, formoterol, guanabenz, guanfacine, hydroxyamphetamine, isoetharine, isoproterenol, isotharine, mephenterine, metaraminol, methamphetamine, methoxamine, methpentermine, methyldopa, methylphenidate, metaproterenol, metaraminol, mitodrine, naphazoline, norepinephrine, oxymetazoline, pemoline, phenylephrine, phenylethylamine, phenylpropanolamine, pirbuterol, prenalterol, procaterol, propylhexedrine, pseudoephedrine, ritodrine, salbutamol, salmeterol, terbutaline, tetrahydrozoline, tramazoline, tyramine and xylometazoline.

2) Adrenergic antagonists such as, for example, acebutolol, alfuzosin, atenolol, betaxolol, bisoprolol, bopindolol, bucindolol, bunazosin, butyrophenones, carteolol, carvedilol, celiprolol, chlorpromazine, doxazosin, ergot alkaloids, esmolol, haloperidol, indoramin, ketanserin, labetalol, levobunolol, medroxalol, metipranolol, metoprolol, nebivolol, nadolol, naftopidil, oxprenolol, penbutolol, phenothiazines, phenoxybenzamine, phentolamine, pindolol, prazosin, propafenone, propranolol, sotalol, tamsulosin, terazosin, timolol, tolazoline, trimazosin, urapidil and yohimbine.

3) Adrenergic neurone blockers such as, for example, bethanidine, debrisoquine, guabenxan, guanadrel, guanazodine, guanethidine, guanoclor and guanoxan.

4) Drugs for treatment of addiction, such as, for example, buprenorphine.

5) Drugs for treatment of alcoholism, such as, for example, disulfuram, naloxone and naltrexone.

6) Drugs for Alzheimer's disease management, including acetylcholinesterase inhibitors such as, for example, donepezil, galantamine, rivastigmine and tacrin.

7) Anaesthetics such as, for example amethocaine, benzocaine, bupivacaine, hydrocortisone, ketamine, lignocaine, methylprednisolone, prilocalne, proxymetacaine, ropivacaine and tyrothricin.

8) Angiotensin converting enzyme inhibitors such as, for example, captopril, cilazapril, enalapril, fosinopril, imidapril hydrochloride, lisinopril, moexipril hydrochloride, perindopril, quinapril, ramipril and trandolapril.

9) Angiotensin II receptor blockers, such as, for example, candesartan, cilexetil, eprosartan, irbesartan, losartan, medoxomil, olmesartan, telmisartan and valsartan.

10) Antiarrhythmics such as, for example, adenosine, amidodarone, disopyramide, flecamide acetate, lidocaine hydrochloride, mexiletine, procainamide, propafenone and quinidine.

11) Antibiotic and antibacterial agents (including the betalactams, fluoroquinolones, ketolides, macrolides, sulphonamides and tetracyclines) such as, for example, aclarubicin, amoxicillin, amphotericin, azithromycin, aztreonam chlorhexidine, clarithromycin, clindamycin, colistimethate, dactinomycin, dirithromycin, doripenem, erythromycin, fusafungine, gentamycin, metronidazole, mupirocin, natamycin, neomycin, nystatin, oleandomycin, pentamidine, pimaricin, probenecid, roxithromycin, sulphadiazine and triclosan.

12) Anti-clotting agents such as, for example, abciximab, acenocoumarol, alteplase, aspirin, bemiparin, bivalirudin, certoparin, clopidogrel, dalteparin, danaparoid, dipyridamole, enoxaparin, epoprostenol, eptifibatide, fondaparin, heparin (including low molecular weight heparin), heparin calcium, lepirudin, phenindione, reteplase, streptokinase, tenecteplase, tinzaparin, tirofiban and warfarin.

13) Anticonvulsants such as, for example, GABA analogs including tiagabine and vigabatrin; barbiturates including pentobarbital; benzodiazepines including alprazolam, chlordiazepoxide, clobazam, clonazepam, diazepam, flurazepam, lorazepam, midazolam, oxazepam and zolazepam; hydantoins including phenyloin; phenyltriazines including lamotrigine; and miscellaneous anticonvulsants including acetazolamide, carbamazepine, ethosuximide, fosphenyloin, gabapentin, levetiracetam, oxcarbazepine, piracetam, pregabalin, primidone, sodium valproate, topiramate, valproic acid and zonisamide.

14) Antidepressants such as, for example, tricyclic and tetracyclic antidepressants including amineptine, amitriptyline (tricyclic and tetracyclic amitryptiline), amoxapine, butriptyline, cianopramine, clomipramine, demexiptiline, desipramine, dibenzepin, dimetacrine, dosulepin, dothiepin, doxepin, imipramine, iprindole, levoprotiline, lofepramine, maprotiline, melitracen, metapramine, mianserin, mirtazapine, nortryptiline, opipramol, propizepine, protriptyline, quinupramine, setiptiline, tianeptine and trimipramine; selective serotonin and noradrenaline reuptake inhibitors (SNRIs) including clovoxamine, duloxetine, milnacipran and venlafaxine; selective serotonin reuptake inhibitors (SSRIs) including citalopram, escitalopram, femoxetine, fluoxetine, fluvoxamine, ifoxetine, milnacipran, nomifensine, oxaprotiline, paroxetine, sertraline, sibutramine, venlafaxine, viqualine and zimeldine; selective noradrenaline reuptake inhibitors (NARIs) including demexiptiline, desipramine, oxaprotiline and reboxetine; noradrenaline and selective serotonin reuptake inhibitors (NASSAs) including mirtazapine; monoamine oxidase inhibitors (MAOIs) including amiflamine, brofaromine, clorgyline, α-ethyltryptamine, etoperidone, iproclozide, iproniazid, isocarboxazid, mebanazine, medifoxamine, moclobemide, nialamide, pargyline, phenelzine, pheniprazine, pirlindole, procarbazine, rasagiline, safrazine, selegiline, toloxatone and tranylcypromine; muscarinic antagonists including benactyzine and dibenzepin; azaspirones including buspirone, gepirone, ipsapirone, tandospirone and tiaspirone; and other antidepressants including acetaphenazine, ademetionine, S-adenosylmethionine, adrafinil, amesergide, amineptine, amperozide, benactyzine, benmoxine, binedaline, bupropion, carbamazepine, caroxazone, cericlamine, cotinine, fezolamine, flupentixol, idazoxan, kitanserin, levoprotiline, lithium salts, maprotiline, medifoxamine, methylphenidate, metralindole, minaprine, nefazodone, nisoxetine, nomifensine, oxaflozane, oxitriptan, phenyhydrazine, roliprame, roxindole, sibutramine, teniloxazine, tianeptine, tofenacin, trazadone, tryptophan, viloxazine and zalospirone.

15) Anticholinergic agents such as, for example, atropine, benzatropine, biperiden, cyclopentolate, glycopyrrolate, hyoscine, ipratropium bromide, orphenadine hydrochloride, oxitroprium bromide, oxybutinin, pirenzepine, procyclidine, propantheline, propiverine, telenzepine, tiotropium, trihexyphenidyl, tropicamide and trospium.

16) Antidiabetic agents such as, for example, pioglitazone, rosiglitazone and troglitazone.

17) Antidotes such as, for example, deferoxamine, edrophonium chloride, fiumazenil, nalmefene, naloxone, and naltrexone.

18) Anti-emetics such as, for example, alizapride, azasetron, benzquinamide, bestahistine, bromopride, buclizine, chlorpromazine, cinnarizine, clebopride, cyclizine, dimenhydrinate, diphenhydramine, diphenidol, domperidone, dolasetron, dronabinol, droperidol, granisetron, hyoscine, lorazepam, metoclopramide, metopimazine, nabilone, ondansetron, palonosetron, perphenazine, prochlorperazine, promethazine, scopolamine, triethylperazine, trifluoperazine, triflupromazine, trimethobenzamide and tropisetron.

19) Antihistamines such as, for example, acrivastine, astemizole, azatadine, azelastine, brompheniramine, carbinoxamine, cetirizine, chlorpheniramine, cinnarizine, clemastine, cyclizine, cyproheptadine, desloratadine, dexmedetomidine, diphenhydramine, doxylamine, fexofenadine, hydroxyzine, ketotifen, levocabastine, loratadine, mizolastine, promethazine, pyrilamine, terfenadine and trimeprazine.

20) Anti-infective agents such as, for example, antivirals (including nucleoside and non-nucleoside reverse transcriptase inhibitors and protease inhibitors) including aciclovir, adefovir, amantadine, cidofovir, efavirenz, famiciclovir, foscarnet, ganciclovir, idoxuridine, indinavir, inosine pranobex, lamivudine, nelfinavir, nevirapine, oseltamivir, palivizumab, penciclovir, pleconaril, ribavirin, rimantadine, ritonavir, ruprintrivir, saquinavir, stavudine, valaciclovir, zalcitabine, zanamivir, zidovudine and interferons; AIDS adjunct agents including dapsone; aminoglycosides including tobramycin; antifungals including amphotericin, caspofungin, clotrimazole, econazole nitrate, fluconazole, itraconazole, ketoconazole, miconazole, nystatin, terbinafine and voriconazole; anti-malarial agents including quinine; antituberculosis agents including capreomycin, ciprofloxacin, ethambutol, meropenem, piperacillin, rifampicin and vancomycin; betalactams including cefazolin, cefmetazole, cefoperazone, cefoxitin, cephacetrile, cephalexin, cephaloglycin and cephaloridine; cephalosporins, including cephalosporin C and cephalothin; cephamycins such as cephamycin A, cephamycin B, cephamycin C, cephapirin and cephradine; leprostatics such as clofazimine; penicillins including amoxicillin, ampicillin, amylpenicillin, azidocillin, benzylpenicillin, carbenicillin, carfecillin, carindacillin, clometocillin, cloxacillin, cyclacillin, dicloxacillin, diphenicillin, heptylpenicillin, hetacillin, metampicillin, methicillin, nafcillin, 2-pentenylpenicillin, penicillin N, penicillin O, penicillin S and penicillin V; quinolones including ciprofloxacin, clinafloxacin, difloxacin, grepafloxacin, norfloxacin, ofloxacine and temafloxacin; tetracyclines including doxycycline and oxytetracycline; miscellaneous anti-infectives including linezolide, trimethoprim and sulfamethoxazole.

21) Anti-neoplastic agents such as, for example, droloxifene, tamoxifen and toremifene.
22) Antiparkisonian drugs such as, for example, amantadine, andropinirole, apomorphine, baclofen, benserazide, biperiden, benztropine, bromocriptine, budipine, cabergoline, carbidopa, eliprodil, entacapone, eptastigmine, ergoline, galanthamine, lazabemide, levodopa, lisuride, mazindol, memantine, mofegiline, orphenadrine, trihexyphenidyl, pergolide, piribedil, pramipexole, procyclidine, propentofylline, rasagiline, remacemide, ropinerole, selegiline, spheramine, terguride and tolcapone.
23) Antipsychotics such as, for example, acetophenazine, alizapride, amisulpride, amoxapine, amperozide, aripiprazole, benperidol, benzquinamide, bromperidol, buramate, butaclamol, butaperazine, carphenazine, carpipramine, chlorpromazine, chlorprothixene, clocapramine, clomacran, clopenthixol, clospirazine, clothiapine, clozapine, cyamemazine, droperidol, flupenthixol, fluphenazine, fluspirilene, haloperidol, loxapine, melperone, mesoridazine, metofenazate, molindrone, olanzapine, penfluridol, pericyazine, perphenazine, pimozide, pipamerone, piperacetazine, pipotiazine, prochlorperazine, promazine, quetiapine, remoxipride, risperidone, sertindole, spiperone, sulpiride, thioridazine, thiothixene, trifluperidol, triflupromazine, trifluoperazine, ziprasidone, zotepine and zuclopenthixol; phenothiazines including aliphatic compounds, piperidines and piperazines; thioxanthenes, butyrophenones and substituted benzamides.
24) Antirheumatic agents such as, for example, diclofenac, heparinoid, hydroxychloroquine and methotrexate, leflunomide and teriflunomide.
25) Anxiolytics such as, for example, adinazolam, alpidem, alprazolam, alseroxlon, amphenidone, azacyclonol, bromazepam, bromisovalum, buspirone, captodiamine, capuride, carbcloral, carbromal, chloral betaine, chlordiazepoxide, clobenzepam, enciprazine, flesinoxan, flurazepam, hydroxyzine, ipsapiraone, lesopitron, loprazolam, lorazepam, loxapine, mecloqualone, medetomidine, methaqualone, methprylon, metomidate, midazolam, oxazepam, propanolol, tandospirone, trazadone, zolpidem and zopiclone.
26) Appetite stimulants such as, for example, dronabinol.
27) Appetite suppressants such as, for example, fenfluramine, phentermine and sibutramine; and anti-obesity treatments such as, for example, pancreatic lipase inhibitors, serotonin and norepinephrine re-uptake inhibitors, and anti-anorectic agents.
28) Benzodiazepines such as, for example, alprazolam, bromazepam, brotizolam, chlordiazepoxide, clobazam, clonazepam, clorazepate, demoxepam, diazepam, estazolam, flunitrazepam, flurazepam, halazepam, ketazolam, loprazolam, lorazepam, lormetazepam, medazepam, midazolam, nitrazepam, nordazepam, oxazepam, prazepam, quazepam, temazepam and triazolam.
29) Bisphosphonates such as, for example, alendronate sodium, sodium clodronate, etidronate disodium, ibandronic acid, pamidronate disodium, isedronate sodium, tiludronic acid and zoledronic acid.
30) Blood modifiers such as, for example, cilostazol and dipyridamol, and blood factors.
31) Cardiovascular agents such as, for example, acebutalol, adenosine, amiloride, amiodarone, atenolol, benazepril, bisoprolol, bumetanide, candesartan, captopril, clonidine, diltiazem, disopyramide, dofetilide, doxazosin, enalapril, esmolol, ethacrynic acid, flecanide, furosemide, gemfibrozil, ibutilide, irbesartan, labetolol, losartan, lovastatin, metolazone, metoprolol, mexiletine, nadolol, nifedipine, pindolol, prazosin, procainamide, propafenone, propranolol, quinapril, quinidine, ramipril, sotalol, spironolactone, telmisartan, tocamide, torsemide, triamterene, valsartan and verapamil.
32) Calcium channel blockers such as, for example, amlodipine, bepridil, diltiazem, felodipine, flunarizine, gallopamil, isradipine, lacidipine, lercanidipine, nicardipine, nifedipine, nimodipine and verapamil.
33) Central nervous system stimulants such as, for example, amphetamine, brucine, caffeine, dexfenfluramine, dextroamphetamine, ephedrine, fenfluramine, mazindol, methylphenidate, modafmil, pemoline, phentermine and sibutramine.
34) Cholesterol-lowering drugs such as, for example, acipimox, atorvastatin, ciprofibrate, colestipol, colestyramine, bezafibrate, ezetimibe, fenofibrate, fluvastatin, gemfibrozil, ispaghula, nictotinic acid, omega-3 triglycerides, pravastatin, rosuvastatin and simvastatin.
35) Drugs for cystic fibrosis management such as, for example, *Pseudomonas aeruginosa* infection vaccines (eg Aerugen™), alpha 1-antitripsin, amikacin, cefadroxil, denufosol, duramycin, glutathione, mannitol, and tobramycin.
36) Diagnostic agents such as, for example, adenosine and aminohippuric acid.
37) Dietary supplements such as, for example, melatonin and vitamins including vitamin E.
38) Diuretics such as, for example, amiloride, bendroflumethiazide, bumetanide, chlortalidone, cyclopenthiazide, furosemide, indapamide, metolazone, spironolactone and torasemide.
39) Dopamine agonists such as, for example, amantadine, apomorphine, bromocriptine, cabergoline, lisuride, pergolide, pramipexole and ropinerole.
40) Drugs for treating erectile dysfunction, such as, for example, apomorphine, apomorphine diacetate, moxisylyte, phentolamine, phosphodiesterase type 5 inhibitors, such as sildenafil, tadalafil, vardenafil and yohimbine.
41) Gastrointestinal agents such as, for example, atropine, hyoscyamine, famotidine, lansoprazole, loperamide, omeprazole and rebeprazole.
42) Hormones and analogues such as, for example, cortisone, epinephrine, estradiol, insulin, Ostabolin-C, parathyroid hormone and testosterone.
43) Hormonal drugs such as, for example, desmopressin, lanreotide, leuprolide, octreotide, pegvisomant, protirelin, salcotonin, somatropin, tetracosactide, thyroxine and vasopressin.
44) Hypoglycaemics such as, for example, sulphonylureas including glibenclamide, gliclazide, glimepiride, glipizide and gliquidone; biguanides including metformin; thiazolidinediones including pioglitazone, rosiglitazone, nateglinide, repaglinide and acarbose.
45) Immunoglobulins.
46) Immunomodulators such as, for example, interferon (e.g. interferon beta-1a and interferon beta-1b) and glatiramer.
47) Immunosupressives such as, for example, azathioprine, cyclosporin, mycophenolic acid, rapamycin, sirolimus and tacrolimus.
48) Mast cell stabilizers such as, for example, cromoglycate, iodoxamide, nedocromil, ketotifen, tryptase inhibitors and pemirolast.
49) Drugs for treatment of migraine headaches such as, for example, almotriptan, alperopride, amitriptyline, amoxapine, atenolol, clonidine, codeine, coproxamol, cyproheptadine, dextropropoxypene, dihydroergotamine, diltiazem, doxepin, ergotamine, eletriptan, fluoxetine, frovatriptan, isomethepene, lidocaine, lisinopril, lisuride, loxapine, methysergide, metoclopramide, metoprolol, nadolol, naratriptan, nortriptyline, oxycodone, paroxetine, pizotifen, pizotyline, prochlorperazine propanolol, propoxyphene, protriptyline, rizatriptan, sertraline, sumatriptan, timolol, tolfenamic acid, tramadol, verapamil, zolmitriptan, and nonsteroidal anti-inflammatory drugs.

50) Drugs for treatment of motion sickness such as, for example, diphenhydramine, promethazine and scopolamine.

51) Mucolytic agents such as N-acetylcysteine, ambroxol, amiloride, dextrans, heparin, desulphated heparin, low molecular weight heparin and recombinant human DNase.

52) Drugs for multiple sclerosis management such as, for example, bencyclane, methylprednisolone, mitoxantrone and prednisolone.

53) Muscle relaxants such as, for example, baclofen, chlorzoxazone, cyclobenzaprine, methocarbamol, orphenadrine, quinine and tizanidine.

54) NMDA receptor antagonists such as, for example, mementine.

55) Nonsteroidal anti-inflammatory agents such as, for example, aceclofenac, acetaminophen, alminoprofen, amfenac, aminopropylon, amixetrine, aspirin, benoxaprofen, bromfenac, bufexamac, carprofen, celecoxib, choline, cinchophen, cinmetacin, clometacin, clopriac, diclofenac, diclofenac sodium, diflunisal, ethenzamide, etodolac, etoricoxib, fenoprofen, flurbiprofen, ibuprofen, indomethacin, indoprofen, ketoprofen, ketorolac, loxoprofen, mazipredone, meclofenamate, mefenamic acid, meloxicam, nabumetone, naproxen, nimesulide, parecoxib, phenylbutazone, piroxicam, pirprofen, rofecoxib, salicylate, sulindac, tiaprofenic acid, tolfenamate, tolmetin and valdecoxib.

56) Nucleic-acid medicines such as, for example, oligonucleotides, decoy nucleotides, antisense nucleotides and other gene-based medicine molecules.

57) Opiates and opioids such as, for example, alfentanil, allylprodine, alphaprodine, anileridine, benzylmorphine, bezitramide, buprenorphine, butorphanol, carbiphene, cipramadol, clonitazene, codeine, codeine phosphate, dextromoramide, dextropropoxyphene, diamorphine, dihydrocodeine, dihydromorphine, diphenoxylate, dipipanone, fentanyl, hydromorphone, L-alpha acetyl methadol, levorphanol, lofentanil, loperamide, meperidine, meptazinol, methadone, metopon, morphine, nalbuphine, nalorphine, oxycodone, papavereturn, pentazocine, pethidine, phenazocine, pholcodeine, remifentanil, sufentanil, tramadol, and combinations thereof with an anti-emetic.

58) Opthalmic preparations such as, for example, betaxolol and ketotifen.

59) Osteoporosis preparations such as, for example, alendronate, estradiol, estropitate, raloxifene and risedronate.

60) Other analgesics such as, for example, apazone, benzpiperylon, benzydamine, caffeine, cannabinoids, clonixin, etoheptazine, flupirtine, nefopam, orphenadrine, pentazocine, propacetamol and propoxyphene.

61) Other anti-inflammatory agents such as, for example, B-cell inhibitors, p38 MAP kinase inhibitors and TNF inhibitors.

62) Phosphodiesterase inhibitors such as, for example, nonspecific phosphodiesterase inhibitors including theophylline, theobromine, IBMX, pentoxifylline and papaverine; phosphodiesterase type 3 inhibitors including bipyridines such as milrinone, aminone and olprinone; imidazolones such as piroximone and enoximone; imidazolines such as imazodan and 5-methyl-imazodan; imidazo-quinoxalines; and dihydropyridazinones such as indolidan and LY181512 (5-(6-oxo-1,4,5,6-tetrahydro-pyridazin-3-yl)-1,3-dihydro-indol-2-one); dihydroquinolinone compounds such as cilostamide, cilostazol, and vesnarinone; motapizone; phosphodiesterase type 4 inhibitors such as cilomilast, etazolate, rolipram, oglemilast, roflumilast, ONO 6126, tolafentrine and zardaverine, and including quinazolinediones such as nitraquazone and nitraquazone analogs; xanthine derivatives such as denbufylline and arofylline; tetrahydropyrimidones such as atizoram; and oxime carbamates such as filaminast; and phosphodiesterase type 5 inhibitors including sildenafil, zaprinast, vardenafil, tadalafil, dipyridamole, and the compounds described in WO 01/19802, particularly (S)-2-(2-hydroxymethyl-1-pyrrolidinyl)-4-(3-chloro-4-methoxy-benzylamino)-5-[N-(2-pyrimidinylmethyl)carbamoyl]pyrimidine, 2-(5,6,7,8-tetrahydro-1,7-naphthyridin-7-yl)-4-(3-chloro-4-methoxybenzylamino)-5-[N-(2-morpholinoethyl)carbamoyl]-pyrimidine, and (S)-2-(2-hydroxymethyl-1-pyrrolidinyl)-4-(3-chloro-4-methoxy-benzylamino)-5-[N-(1,3,5-trimethyl-4-pyrazolyl)carbamoyl]-pyrimidine).

63) Potassium channel modulators such as, for example, cromakalim, diazoxide, glibenclamide, levcromakalim, minoxidil, nicorandil and pinacidil.

64) Prostaglandins such as, for example, alprostadil, dinoprostone, epoprostanol and misoprostol.

65) Respiratory agents and agents for the treatment of respiratory diseases including bronchodilators such as, for example, the β2-agonists bambuterol, bitolterol, broxaterol, carmoterol, clenbuterol, fenoterol, formoterol, indacaterol, levalbuterol, metaproterenol, orciprenaline, picumeterol, pirbuterol, procaterol, reproterol, rimiterol, salbutamol, salmeterol, terbutaline and the like; inducible nitric oxide synthase (iNOS) inhibitors; the antimuscarinics ipratropium, ipratropium bromide, oxitropium, tiotropium, glycopyrrolate and the like; the xanthines aminophylline, theophylline and the like; adenosine receptor antagonists, cytokines such as, for example, interleukins and interferons; cytokine antagonists and chemokine antagonists including cytokine synthesis inhibitors, endothelin receptor antagonists, elastase inhibitors, integrin inhibitors, leukotrine receptor antagonists, prostacyclin analogues, and ablukast, ephedrine, epinephrine, fenleuton, iloprost, iralukast, isoetharine, isoproterenol, montelukast, ontazolast, pranlukast, pseudoephedrine, sibenadet, tepoxalin, verlukast, zafirlukast and zileuton.

66) Sedatives and hypnotics such as, for example, alprazolam, butalbital, chlordiazepoxide, diazepam, estazolam, flunitrazepam, flurazepam, lorazepam, midazolam, temazepam, triazolam, zaleplon, zolpidem, and zopiclone.

67) Serotonin agonists such as, for example, 1-(4-bromo-2,5-dimethoxyphenyl)-2-aminopropane, buspirone, m-chlorophenylpiperazine, cisapride, ergot alkaloids, gepirone, 8-hydroxy-(2-N,N-dipropylamino)-tetraline, ipsaperone, lysergic acid diethylamide, 2-methyl serotonin, mezacopride, sumatriptan, tiaspirone, trazodone and zacopride.

68) Serotonin antagonists such as, for example, amitryptiline, azatadine, chlorpromazine, clozapine, cyproheptadine, dexfenfluramine, R(+)-α-(2,3-dimethoxyphenyl)-1-[2-(4-fluorophenyl)ethyl]-4-piperidine-methanol, dolasetron, fenclonine, fenfluramine, granisetron, ketanserin, methysergide, metoclopramide, mianserin, ondansetron, risperidone, ritanserin, trimethobenzamide and tropisetron.

69) Steroid drugs such as, for example, alcometasone, beclomethasone, beclomethasone dipropionate, betamethasone, budesonide, butixocort, ciclesonide, clobetasol, deflazacort, diflucortolone, desoxymethasone, dexamethasone, fludrocortisone, flunisolide, fluocinolone, fluometholone, fluticasone, fluticasone proprionate, hydrocortisone, methylprednisolone, mometasone, nandrolone decanoate, neomycin sulphate, prednisolone, rimexolone, rofleponide, triamcinolone and triamcinolone acetonide.

70) Sympathomimetic drugs such as, for example, adrenaline, dexamfetamine, dipirefin, dobutamine, dopamine, dopexamine, isoprenaline, noradrenaline, phenylephrine, pseudoephedrine, tramazoline and xylometazoline.
71) Nitrates such as, for example, glyceryl trinitrate, isosorbide dinitrate and isosorbide mononitrate.
72) Skin and mucous membrane agents such as, for example, bergapten, isotretinoin and methoxsalen.
73) Smoking cessation aids such as, for example, bupropion, nicotine and varenicline.
74) Drugs for treatment of Tourette's syndrome such as, for example, pimozide.
75) Drugs for treatment of urinary tract infections such as, for example, darifenicin, oxybutynin, propantheline bromide and tolteridine.
76) Vaccines.
77) Drugs for treating vertigo such as, for example, betahistine and meclizine.
78) Therapeutic proteins and peptides such as acylated insulin, glucagon, glucagon-like peptides, exendins, insulin, insulin analogues, insulin aspart, insulin detemir, insulin glargine, insulin glulisine, insulin lispro, insulin zinc, isophane insulins, neutral, regular and insoluble insulins, and protamine zinc insulin.
79) Anticancer agents such as, for example, anthracyclines, doxorubicin, idarubicin, epirubicin, methotrexate, taxanes, paclitaxel, docetaxel, cisplatin, vinca alkaloids, vincristine and 5-fluorouracil.
80) Pharmaceutically acceptable salts or derivatives of any of the foregoing.

It should be noted that drugs listed above under a particular indication or class may also find utility in other indications. A plurality of active agents can be employed in the practice of the present invention. A drug delivery system according to the invention may also be used to deliver combinations of two or more different active agents or drugs. Specific combinations of two medicaments which may be mentioned include combinations of steroids and $\beta_2$-agonists. Examples of such combinations are beclomethasone and formoterol; beclomethasone and salmeterol; fluticasone and formoterol; fluticasone and salmeterol; budesonide and formoterol; budesonide and salmeterol; flunisolide and formoterol; flunisolide and salmeterol; ciclesonide and formoterol; ciclesonide and salmeterol; mometasone and formoterol; and mometasone and salmeterol. Specifically drug delivery systems according to the invention may also be used to deliver combinations of three or more different active agents or drugs.

It will be clear to a person of skill in the art that, where appropriate, the active agents or drugs may be linked to a carrier molecule or molecules and/or used in the form of prodrugs, salts, as esters, or as solvates to optimise the activity and/or stability of the active agent or drug. The device used to deliver the formulation will clearly affect the performance of the formulations and the device is therefore a very important part of present invention.

As mentioned above, in order to maintain the physical form of an active substance, a protective coating may be applied to the external surfaces of the particles comprising the active agent. Several methods are known for applying such coatings.

Compressive Milling Processes

In an alternative process for preparing the compositions according to the present invention, the powder components undergo a compressive milling process, such as processes termed mechanofusion (also known as 'Mechanical Chemical Bonding') and cyclomixing.

As the name suggests, mechanofusion is a dry coating process designed to mechanically fuse a first material onto a second material. It should be noted that the use of the terms "mechanofusion" and "mechanofused" are supposed to be interpreted as a reference to a particular type of milling process, but not a milling process performed in a particular apparatus. The compressive milling processes work according to a different principle to other milling techniques, relying on a particular interaction between an inner element and a vessel wall, and they are based on providing energy by a controlled and substantial compressive force. The process works particularly well where one of the materials is generally smaller and/or softer than the other.

The fine active particles and additive particles are fed into the vessel of a mechanofusion apparatus (such as a Mechano-Fusion system (Hosokawa Micron Ltd), where they are subject to a centrifugal force and are pressed against the vessel inner wall. The powder is compressed between the fixed clearance of the drum wall and a curved inner element with high relative speed between drum and element. The inner wall and the curved element together form a gap or nip in which the particles are pressed together. As a result, the particles experience very high shear forces and very strong compressive stresses as they are trapped between the inner drum wall and the inner element (which has a greater curvature than the inner drum wall). The particles are pressed against each other with enough energy to locally heat and soften, break, distort, flatten and wrap the additive particles around the core particle to form a coating. The energy is generally sufficient to break up agglomerates and some degree of size reduction of both components may occur.

These mechanofusion and cyclomixing processes apply a high enough degree of force to separate the individual particles of active material and to break up tightly bound agglomerates of the active particles such that effective mixing and effective application of the additive material to the surfaces of those particles is achieved. An especially desirable aspect of the processes is that the additive material becomes deformed in the milling and may be smeared over or fused to the surfaces of the active particles.

However, in practice, these compression milling processes produce little or no size reduction of the drug particles, especially where they are already in a micronised form (i.e. <10 μm). The only physical change which may be observed is a plastic deformation of the particles to a rounder shape.

Other Milling Procedures

The process of milling may also be used to formulate the dry powder compositions according to the present invention. The manufacture of fine particles by milling can be achieved using conventional techniques. In the conventional use of the word, "milling" means the use of any mechanical process which applies sufficient force to the particles of active material that it is capable of breaking coarse particles (for example, particles with a MMAD greater than 100 μm) down to fine particles (for example, having a MMAD not more than 50 μm). In the present invention, the term "milling" also refers to deagglomeration of particles in a formulation, with or without particle size reduction. The particles being milled may be large or fine prior to the milling step. A wide range of milling devices and conditions are suitable for use in the production of the compositions of the inventions. The selection of appropriate milling conditions, for example, intensity of milling and duration, to provide the required degree of force will be within the ability of the skilled person.

Impact milling processes may be used to prepare compositions comprising apomorphine according to the present invention, with or without additive material. Such processes include ball milling and the use of a homogenizer.

Ball milling is a suitable milling method for use in the prior art co-milling processes. Centrifugal and planetary ball milling are especially preferred methods.

Alternatively, a high pressure homogeniser may be used in which a fluid containing the particles is forced through a valve at high pressure producing conditions of high shear and turbulence. Shear forces on the particles, impacts between the particles and machine surfaces or other particles, and cavitation due to acceleration of the fluid may all contribute to the fracture of the particles. Suitable homogenisers include EmulsiFlex high pressure homogenisers which are capable of pressures up to 4000 bar, Niro Soavi high pressure homogenisers (capable of pressures up to 2000 bar), and Microfluidics Microfluidisers (maximum pressure 2750 bar). The milling process can be used to provide the microparticles with mass median aerodynamic diameters as specified above. Homogenisers may be more suitable than ball mills for use in large scale preparations of the composite active particles.

The milling step may, alternatively, involve a high energy media mill or an agitator bead mill, for example, the Netzsch high energy media mill, or the DYNO-mill (Willy A. Bachofen AG, Switzerland).

If a significant reduction in particle size is also required, co-jet milling is preferred, as disclosed in the earlier patent application published as WO 2005/025536. The co-jet milling process can result in composite active particles with low micron or sub-micron diameter, and these particles exhibit particularly good FPF and FPD, even when dispensed using a passive DPI.

The milling processes apply a high enough degree of force to break up tightly bound agglomerates of fine or ultra-fine particles, such that effective mixing and effective application of the additive material to the surfaces of those particles is achieved. These impact processes create high-energy impacts between media and particles or between particles. In practice, while these processes are good at making very small particles, it has been found that neither the ball mill nor the homogenizer was particularly effective in producing dispersion improvements in resultant drug powders in the way observed for the compressive process. It is believed that the second impact processes are not as effective in producing a coating of additive material on each particle.

Conventional methods comprising co-milling active material with additive materials (as described in WO 02/43701) result in composite active particles which are fine particles of active material with an amount of the additive material on their surfaces. The additive material is preferably in the form of a coating on the surfaces of the particles of active material. The coating may be a discontinuous coating. The additive material may be in the form of particles adhering to the surfaces of the particles of active material. Co-milling or co-micronising particles of active agent and particles of additive (FCA) or excipient will result in the additive or excipient becoming deformed and being smeared over or fused to the surfaces of fine active particles, producing composite particles made up of both materials. These resultant composite active particles comprising an additive have been found to be less cohesive after the milling treatment.

At least some of the composite active particles may be in the form of agglomerates. However, when the composite active particles are included in a pharmaceutical composition, the additive material promotes the dispersal of the composite active particles on administration of that composition to a patient, via actuation of an inhaler.

Milling may also be carried out in the presence of a material which can delay or control the release of the active agent.

The co-milling or co-micronising of active and additive particles may involve compressive type processes, such as mechanofusion, cyclomixing and related methods such as those involving the use of a Hybridiser or the Nobilta. The principles behind these processes are distinct from those of alternative milling techniques in that they involve a particular interaction between an inner element and a vessel wall, and in that they are based on providing energy by a controlled and substantial compressive force, preferably compression within a gap of predetermined width.

In one embodiment, if required, the microparticles produced by the milling step can then be formulated with an additional excipient. This may be achieved by a spray drying process, e.g. co-spray drying (Need to expand). In this embodiment, the particles are suspended in a solvent and co-spray dried with a solution or suspension of the additional excipient. Preferred additional excipients include polysaccharides. Additional pharmaceutical effective excipients may also be used.

In another embodiment, the powder compositions are produced using the two-step process. Firstly, the materials are milled or blended. Next, they undergo mechanofusion and this mechanofusion step is thought to "polish" the composite active particles, further rubbing the additive material into the active particles. This allows one to enjoy the beneficial properties afforded to particles by mechanofusion, in combination with the very small particles sizes made possible by the co-jet milling.

The reduction in the cohesion and adhesion between the active particles can lead to equivalent performance with reduced agglomerate size, or even with individual particles.

High Shear Blending

Scaling up of pharmaceutical product manufacture often requires the use one piece of equipment to perform more than one function. An example of this is the use of a mixer-granulator which can both mix and granulate a product thereby removing the need to transfer the product between pieces of equipment. In so doing, the opportunity for powder segregation is minimised. High shear blending often uses a high-shear rotor/stator mixer (HSM), which has become used in mixing applications. Homogenizers or "high shear material processors" develop a high pressure on the material whereby the mixture is subsequently transported through a very fine orifice or comes into contact with acute angles. The flow through the chambers can be reverse flow or parallel flow depending on the material being processed. The number of chambers can be increased to achieve better performance. The orifice size or impact angle may also be changed for optimizing the particle size generated. Particle size reduction occurs due to the high shear generated by the high shear material processors while it passes through the orifice and the chambers. The ability to apply intense shear and shorten mixing cycles gives these mixers broad appeal for applications that require agglomerated powders to be evenly blended. Furthermore conventional HSMs may also be widely used for high intensity mixing, dispersion, disintegration, emulsification and homogenization.

It is well known to those skilled in the production of powder formulations that small particles, even with high-power, high-shear, mixers a relatively long period of "aging" is required to obtain complete dispersion, and this period is not shortened appreciably by increases in mixing power, or by increasing the speed of rotation of the stirrer so as to increase the shear velocity. High shear mixers can also be used if the auto-adhesive properties of the drug particles are so that high shear forces are required together with use of a force-controlling agent for forming a surface-energy-reducing particulate coating or film.

Spray Drying and Ultrasonic Nebulisers

Spray drying may be used to produce particles of inhalable size comprising the active and excipient. The spray drying process may be adapted to produce spray-dried particles that include active agent and additive material which promotes formulation stability and controls the agglomeration of particles and powder performance. The spray drying process may also be adapted to produce spray-dried particles that include the active agent dispersed or suspended within a material that provides the controlled release properties.

Spray drying is a well-known and widely used technique for producing particles of active material of inhalable size. Conventional spray drying techniques may be improved so as to produce active particles with enhanced chemical and physical properties so that they perform better when dispensed from a DPI than particles formed using conventional spray drying techniques. Such improvements are described in detail in the earlier patent application published as WO 2005/025535.

In particular, it is disclosed that co-spray drying an active agent with an FCA under specific conditions can result in particles with excellent properties which perform extremely well when administered by a DPI for inhalation into the lung.

It has been found that manipulating or adjusting the spray drying process can result in the FCA being largely present on the surface of the particles. That is, the FCA is concentrated at the surface of the particles, rather than being homogeneously distributed throughout the particles. This clearly means that the FCA will be able to reduce the tendency of the particles to agglomerate. This will assist the formation of unstable agglomerates that are easily and consistently broken up upon actuation of a DPI.

It has been found that it may be advantageous to control the formation of the droplets in the spray drying process, so that droplets of a given size and of a narrow size distribution are formed. Furthermore, controlling the formation of the droplets can allow control of the air flow around the droplets which, in turn, can be used to control the drying of the droplets and, in particular, the rate of drying. Controlling the formation of the droplets may be achieved by using alternatives to the conventional 2-fluid nozzles, especially avoiding the use of high velocity air flows. In particular, it is preferred to use a spray drier comprising a means for producing droplets moving at a controlled velocity and of a predetermined droplet size. The velocity of the droplets is preferably controlled relative to the body of gas into which they are sprayed. This can be achieved by controlling the droplets' initial velocity and/or the velocity of the body of gas into which they are sprayed, for example by using an ultrasonic nebuliser (USN) to produce the droplets. Alternative nozzles such as electrospray nozzles or vibrating orifice nozzles may be used.

In one embodiment, an ultrasonic nebuliser (USN) is used to form the droplets in the spray mist. USNs use an ultrasonic transducer which is submerged in a liquid. The ultrasonic transducer (a piezoelectric crystal) vibrates at ultrasonic frequencies to produce the short wavelengths required for liquid atomisation. In one common form of USN, the base of the crystal is held such that the vibrations are transmitted from its surface to the nebuliser liquid, either directly or via a coupling liquid, which is usually water. When the ultrasonic vibrations are sufficiently intense, a fountain of liquid is formed at the surface of the liquid in the nebuliser chamber. Droplets are emitted from the apex and a "fog" emitted.

Whilst ultrasonic nebulisers (USNs) are known, these are conventionally used in inhaler devices, for the direct inhalation of solutions containing drug, and they have not previously been widely used in a spray drying apparatus. It has been discovered that the use of such a nebuliser in spray drying has a number of important advantages and these have not previously been recognised. The preferred USNs control the velocity of the particles and therefore the rate at which the particles are dried, which in turn affects the shape and density of the resultant particles. The use of USNs also provides an opportunity to perform spray drying on a larger scale than is possible using conventional spray drying apparatus with conventional types of nozzles used to create the droplets, such as 2-fluid nozzles.

The attractive characteristics of USNs for producing fine particle dry powders include: low spray velocity; the small amount of carrier gas required to operate the nebulisers; the comparatively small droplet size and narrow droplet size distribution produced; the simple nature of the USNs (the absence of moving parts which can wear, contamination, etc.); the ability to accurately control the gas flow around the droplets, thereby controlling the rate of drying; and the high output rate which makes the production of dry powders using USNs commercially viable in a way that is difficult and expensive when using a conventional two-fluid nozzle arrangement.

USNs do not separate the liquid into droplets by increasing the velocity of the liquid. Rather, the necessary energy is provided by the vibration caused by the ultrasonic nebuliser.

Rather than pressurising the liquid, rotary atomisers use the centrifugal energy created by a spinning disc or receptacle to form droplets. Pressure based systems are somewhat limited in their ability to create a droplet spectrum with a narrow distribution and high kurtosis value. Additionally, rotary atomisers are not limited by flow volume and are capable of operating effectively at very low volumes.

Electrohydrodynamic (EHD) atomization requires the use of electrical forces to assist in the dispersion of a fluid due. Conventional EHD atomization, forces a conductive fluid through an electrically conductive nozzle. The nozzle is connected to a high negative voltage, whereby an electric field is created between the conductive nozzle and a ground electrode. This field is strongest at the tip of the nozzle. As the fluid exits the nozzle, electrical and mechanical forces cause the fluid jet to nebulise. The resulting droplets are further influences by the properties of the fluid for example surface tension, electrical conductivity, viscosity, density and viscoelastic behaviour. Further operational parameters may be varied such as the rate of flow and the local electric field to assist in obtaining the desired droplets. When the fluid jet is sent in the direction of an electrically grounded target or towards a target with either a potential of opposite polarity, or a potential lower than that of the jet, the droplets are attracted to and will deposit on the target.

Delivery Devices

The inhalable compositions in accordance with the present invention are preferably administered via a pressurized metered dose inhaler (pMDI), or even via a nebulised system.

In a yet further embodiment, the composition is a solution or suspension and is administered using a pressurised metered dose inhaler (pMDI), a nebuliser or a soft mist inhaler. Examples of suitable devices include pMDIs such as Modulite® (Chiesi), SkyeFine™ and SkyeDry™ (SkyePharma). Nebulisers such as Porta-Neb®, Inquaneb™ (Pari) and Aquilon™, and soft mist inhalers such as eFlow™ (Pari), Aerodose™ (Aerogen), Respimat® Inhaler (Boehringer Ingelheim GmbH), AERx® Inhaler (Aradigm) and Mystic™ (Ventaira Pharmaceuticals, Inc.).

In embodiments of the present invention, the propellant is CFC-12 or an ozone-friendly, non-CFC propellant, such as 1,1,1,2-tetrafluoroethane (HFC 134a), 1,1,1,2,3,3,3-heptafluoropropane (HFC-227), HCFC-22 (difluororchloromethane), HFA-152 (difluoroethane and isobutene) or combinations thereof. Such formulations may require the inclusion of a polar surfactant such as polyethylene glycol, diethylene glycol monoethyl ether, polyoxyethylene sorbitan monolaurate, polyoxyethylene sorbitan monooleate, propoxylated polyethylene glycol, and polyoxyethylene lauryl ether for suspending, solubilising, wetting and emulsifying the active agent and/or other components, and for lubricating the valve components of the MDI.

Improving Percentage FPF in the Drug Formulation

The present disclosure also relates to the use of vinyl polymers such as Vinylpyrrolidone Homopolymers and Copolymers, and in particular polyvinylpyrrolidone (PVP), in improving the % FPF of a drug particle during storage.

In one aspect the invention relates to use of vinyl polymers, in particular PVP, in the preparation of a medicament which has an increase in % FPF from time 0 (the date of formulation) to at least week 7 of storage. In a further aspect the invention relates to a pharmaceutical composition comprising a vinyl polymer, in particular PVP, suitably which have enhanced % FPF after storage.

The present invention further relates to a method for manufacture of a drug for inhalation, the method comprising formulating the drug with a vinyl polymer and storing the formulation to allow a suitable fine particle fraction to be obtained.

In the yet further aspect the invention relates to use of PVP in the manufacturer of a medicament for inhalation.

General Statements

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine study, numerous equivalents to the specific procedures described herein. Such equivalents are considered to be within the scope of this invention and are covered by the claims. All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference. The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects. As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof as used herein refers to all permutations and combinations of the listed items preceding the term. For example, "A, B, C, or combinations thereof is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

The preferred embodiments, as described for different aspects of the invention, are the same for other aspects of the invention mutatis mutandis The present invention is illustrated by the by the experimental data set out below, which is not limiting upon the invention, wherein:

EXAMPLES

The following examples are provided to illustrate the invention but should not be construed as limiting the invention. Particle size, respirable fraction, and medication delivery are determined using the test methods described below.

The spray dried powders were characterised by particle size using a Sympatec laser sizer, infra-red spectroscopy using a Perkin Elmer Spectrum GX ATR-FTIR, and thermal behaviour using a Perkin Elmer Diamond differential scanning calorimeter.

Spray Drying Parameters:
Vessel Type: Cyclone (1"/3")
Pump setting: 87 rpm
Tubing: 1.6 mm
Feed rate: 5 g/min
Inlet temp: 120° C.
Atomisation Type: 2FN
Atomisation Pressure: 3.0 bar g
Atomisation Air Flow: 30 l/min
Drying air pressure: 1.0 bar g
Drying airflow 4.5 l/min The above spray drying process was repeated for different tiotropium bromide/trehalose/leucine combinations outlined below.

Manufacturing

Conventional manufacturing methods and machinery well known to those skilled in the art of pharmaceutical aerosol manufacture were employed for the preparation of pMDI batches. A known mass of spray dried active (or combinations of active with trehalose and/or leucine) were dispensed into an empty canister, a metering valve was crimped on, and the propellant/excipient mixture was filled into the canister through the valve. The cans were ultrasonicated and inverted to mix.

Each filled canister was conveniently fitted into a suitable channelling device prior to use to form a metered dose inhaler for administration of the medicament into the lungs of a patient. Suitable channelling devices comprise, for example a valve actuator and a cylindrical or cone-like passage through which medicament may be delivered from the filled canister via the metering valve to the mouth of a patient e.g., a mouthpiece actuator.

In a typical arrangement the valve stem is seated in a nozzle block which has an orifice leading to an expansion chamber. The expansion chamber has an exit orifice which extends into the mouthpiece. Actuator (exit) orifice diameters in the range 0.15-0.45 mm especially 0.2-0.45 mm are generally suitable e.g., 0.25, 0.30, 0.33 or 0.42 mm. An orifice diameter of 0.22 mm is also suitable.

Characterisation

The spray dried powders were characterised by particle size using a Sympatec laser sizer, infra-red spectroscopy using a Perkin Elmer Spectrum GX ATR-FTIR, and thermal behaviour using a Perkin Elmer Diamond differential scanning calorimeter.

Particle Size Assay:

Metered dose(s) of the aerosol formulation are actuated into an Anderson Cascade Impactor (ACI) (available from Westtech) equipped with a USP throat using a Bespak 0.36 mm actuator for an aerosol valve. The particle size distribution of the resulting suspension was then analyzed using a bespoke HPLC assay.

The aerosol vial to be tested was shaken and primed 5 times into a vented area away from the analyzer.

The Shot Weight and Delivered Dose and their variance were measured using the Dosage Unit Sampling Apparatus (DUSA). The fine particle fraction (FPF) was measured using an Andersen Cascade Impactor (ACI). The measurement methodology and the apparatus are well known in the art, and are described in the United States Pharmacopoeia (USP) Chapter <601>, or in the inhalants monograph of the European Pharmacopoeia (EP), both of which are hereby incorporated by reference. The USP states that Delivered Dose Uniformity should be measured with DUSA or its equivalent and the dose determined using HPLC analysis.

Fine particle fraction measured according to the above described methodology is considered to be the combined fractions collected from the stages of an Andersen Cascade Impactor calibrated at 28.3 l/min air flow rate. These fractions have an aerodynamic particle size of less than 5 p.m.

The Andersen Cascade Impactor was assembled according to manufacturer's instructions with a suitable filter in place to ensure that the system was airtight. The apparatus was connected to a flow system comprising flow control valve, two-way valve, timer and vacuum pump.

The test was conducted at a flow rate of 28.3 l/min. The flow rate was adjusted by connecting a flow meter, calibrated for the volumetric flow leaving the meter, to the induction port. If necessary, the flow control valve was adjusted to achieve steady flow through the system at the required rate.

The metered dose inhaler was prepared for use by placing in a Bespak BK356 series actuator. With the pump running and the two-way valve open, the inhaler was shaken and the mouthpiece of the inhaler was engaged in the mouthpiece adapter. The aerosol was discharged into the apparatus by opening the actuating for 3 seconds before releasing the valve. The discharge sequence was repeated 3 times.

The number of discharges should be minimised and typically would not be greater than ten. The number of discharges should be sufficient to ensure an accurate and precise determination of fine particle dose. Between discharges, wait for 1 minute and then switch off the pump.

The apparatus was dismantled and the filter was carefully removed. The active ingredient was extracted into an aliquot of the solvent. The throat and mouthpiece adapter were removed from the apparatus and the drug was extracted into an aliquot of the solvent. The active ingredient was extracted from the USP throat into an aliquot of the solvent. The active ingredient was extracted from the inner walls and the collection plates of each of the stages of the apparatus into aliquots of solvent. Using a suitable method of analysis, the quantity of active ingredient contained in each of the ten volumes of solvent was determined.

The mass of active ingredient deposited on each stage per discharge and the mass of active ingredient per discharge deposited in the actuator, USP throat and mouthpiece adapter were calculated The aerosol vial to be tested was primed five times. The aerosol vial and a clean, dry actuator were coupled to the USP throat attached to the top of the impactor using an appropriate firing adapter. The calibrated vacuum pump (28.3 L/min) was attached to the cascade impactor and turned on. A total of 10 sprays were delivered into the cascade impactor by repeatedly shaking the vial and then immediately delivering a single spray. The time between sprays was approximately 60 seconds. The cascade impactor was disassembled and each component was rinsed separately with diluent (15 parts of methanol mixed with 85 parts water and 0.1 parts trifluoroacetic acid, v/v). Each solution was analyzed for active content using high pressure liquid chromatography.

The respirable fraction was calculated using CITDAS software, version 2.0 (Copley Scientific, UK).

Storage/Stability

Samples of each formulation 1-4 (100 mg) were stored at room temperature and low relative humidity (RH) (20-30%) in 7 ml screw top vials sealed with Parafilm and the characterisation repeated after 9 and 14 days.

Differential Scanning Calorimetry

The sample (5 to 10 mg) was sealed in a pierced 40 µl aluminium sample pan and heated from 25 to 250° C. at 50° C. per minute.

Infra-Red Spectroscopy

The absorbance spectra were measured using the Golden Gate Attenuated Total Reflectance (ATR) accessory between 4000 and 600 $cm^{-1}$ acquiring 16 co-added scans. The spectra were compared with that of the crystalline staring materials and between time points.

Spectra were recorded at 9 and 14 days and demonstrated no differences in position or intensity of any of the peaks from those recorded on the day of manufacture. Comparison of the spectra with those of the starting materials indicate that the formulations are amorphous in that sharp peaks seen above 3000 $cm^{-1}$ for crystalline tiotropium bromide and trehalose dihydrate are absent from the sample spectra. The fingerprint regions in the spectra are too complex to allow clear assignment of any of the peaks.

Example 1

Control—Crystalline

Tiotropium bromide (3.8 mg) was added into a coated (DuPont 3200 200) canister, with Bespak 63 µl valve. HFA 134a (14700 mg) was added to the canister. The solution was shaken.

Anderson Cascade Impactor (ACI)

| | |
|---|---|
| Delivered Dose (µg) | 18.1 |
| FPD (µg) | 0.5 |
| FPF (%) | 2.8 |

| | |
|---|---|
| MMAD (μm) | 11.5 |
| GSD | 1.8 |

Example 2

Control—Spray Dried

Spray dried tiotropium bromide (3.8 mg) was added into a coated (DuPont 3200 200) canister, with Bespak 63 μl valve. HFA 134a (14700 mg) was added to the canister. The solution was shaken.
Anderson Cascade Impactor (ACI)

| | |
|---|---|
| Delivered Dose (μg) | 18.1 |
| FPD (μg) | 0.4 |
| FPF (%) | 2.2 |
| MMAD (μm) | 11.4 |
| GSD | 1.8 |

Example 3

Formulation 1 (Tiotropium Bromide:Trehalose:Leucine 50:25:25 Wt %)

Tiotropium bromide (1.2 g), trehalose dehydrate (0.6 g), and L-leucine (0.6 g) were dissolved into methanol (60 ml). The solutions were combined by shaking. Water (60 ml) was added and shaken until dissolution occurred. The resultant solution was spray dried according to the parameters outlined above.
Bulk Particle Size Data—Sympatec Data

TABLE 3

| Formulation 1: | | | | |
|---|---|---|---|---|
| | X10 (μm) | X50 (μm) | X90 (μm) | X99 (μm) |
| 0 days | 0.56 | 1.15 | 2.10 | 3.96 |
| 9 days | 0.49 | 1.12 | 2.12 | 3.84 |
| 14 days | 0.51 | 1.13 | 2.12 | 3.95 |

Bulk DSC Data
T=0 days Tg=70° C., no other events
T=9 days Tg=63° C., broad re-crystallisation followed by melting with decomposition above 200° C.
T=14 days Tg=61° C., broad re-crystallisation followed by melting with decomposition above 200° C.
T=35 days Tg=61° C., broad re-crystallisation followed by melting with decomposition above 200° C.
Formulation A
Spray dried tiotropium bromide:trehalose:leucine 50:25:25 wt % (6.3 mg) was added into a coated (DuPont 3200 200) canister, with Bespak 63 μl valve. HFA 227 (14300 mg) was added to the canister. The solution was shaken.
Anderson Cascade Impactor

| | |
|---|---|
| Delivered Dose (μg) | 10.6 |
| FPD (μg) | 4.6 |
| FPF (%) | 43.8 |
| MMAD (μm) | 2.8 |
| GSD | NA |

Formulation B
Spray dried tiotropium bromide:trehalose:leucine 50:25:25 wt % (6.3 mg) was added into a coated (DuPont 3200 200) canister, with Bespak 63 μl valve. HFA 227 with 0.1% w/w Abs Ethanol (14200 mg) was added to the canister. The suspension was shaken.
Anderson Cascade Impactor

| | |
|---|---|
| Delivered Dose (μg) | 13.5 |
| FPD (μg) | 4.1 |
| FPF (%) | 30.7 |
| MMAD (μm) | 4.2 |
| GSD | 2.4 |

Example 4

Formulation 2 (Tiotropium Bromide:Trehalose:Leucine 75:15:15 Wt %)

Tiotropium bromide (1.4 g), trehalose dehydrate (0.3 g) and L-leucine (0.3 g) were dissolved into methanol (60 ml). The solution was shaken. Water (60 ml) was added and shaken until dissolution occurred. The resultant solution was spray dried according to the parameters outlined below.
Bulk Particle Size Data—Synpatec Data

TABLE 4

| Formulation 2 | | | | |
|---|---|---|---|---|
| | X10 (μm) | X50 (μm) | X90 (μm) | X99 (μm) |
| 0 days | 0.63 | 1.25 | 2.23 | 3.54 |
| 9 days | 0.60 | 1.23 | 2.23 | 3.59 |
| 14 days | 0.59 | 1.21 | 2.19 | 3.62 |

Bulk DSC Data
T=0 days Tg=69° C., no other events
T=9 days Tg=59° C., small re-crystallisation followed by melting with decomposition above 200° C.
T=14 days Tg=72° C. with no other clear transitions, decomposition above 200° C.
T=35 days Tg=54° C., broad re-crystallisation followed by melting with decomposition above 200° C.
Formulation A
Spray dried tiotropium bromide:trehalose:leucine 75:15:15 wt % (4.5 mg) was added into a coated (DuPont 3200 200) canister, with Bespak 63 μl valve. HFA 227 (14300 mg) was added to the canister. The solution was shaken.
Anderson Cascade Impactor

| | |
|---|---|
| Delivered Dose (μg) | 10.7 |
| FPD (μg) | 6.7 |
| FPF (%) | 62.0 |
| MMAD (μm) | 2.8 |
| GSD | 1.8 |

Formulation B
Spray dried tiotropium bromide:trehalose:leucine 75:15:15 wt % (4.48 mg) was added into a coated (DuPont 3200 200) canister, with Bespak 63 μl valve. HFA 227 with 0.1% w/w Abs Ethanol (14200 mg) was added to the canister. The suspension was shaken.

Anderson Cascade Impactor

| | |
|---|---|
| Delivered Dose (µg) | 11.2 |
| FPD (µg) | 5.8 |
| FPF (%) | 51.6 |
| MMAD (µm) | 2.9 |
| GSD | 2.1 |

Example 5

Formulation 3 (Tiotropium Bromide:Leucine 75:25 Wt %)

Tiotropium bromide (1.4 g) and L-leucine (0.5 g) were dissolved into methanol (60 ml). Water (60 ml) was added and shaken until dissolution occurred. The resultant solution was spray dried according to the parameters outlined above.
Bulk Particle Size Data—Sympatec Data

TABLE 5

| | Formulation 3 | | | |
|---|---|---|---|---|
| | X10 (µm) | X50 (µm) | X90 (µm) | X99 (µm) |
| 0 days | 0.74 | 1.41 | 2.53 | 3.78 |
| 9 days | 0.73 | 1.39 | 2.52 | 4.33 |
| 14 days | 0.72 | 1.39 | 2.50 | 4.53 |

Bulk DSC Data
T=0 days Tg=64° C., no other events
T=9 days Tg=77° C., broad re-crystallisation followed by melting with decomposition above 200° C.
T=14 days Tg=64° C., broad re-crystallisation followed by melting with decomposition above 200° C.
T=35 days Tg=64° C., broad re-crystallisation followed by melting with decomposition above 180° C.

Formulation A

Spray dried tiotropium bromide:leucine 75:25 wt % (4.2 mg) was added into a coated (DuPont 3200 200) canister, with Bespak 63 µl valve. HFA 227 (14300 mg) was added to the canister. The solution was shaken.
Anderson Cascade Impactor

| | |
|---|---|
| Delivered Dose (µg) | 10.5 |
| FPD (µg) | 6.2 |
| FPF (%) | 59.0 |
| MMAD (µm) | 2.7 |
| GSD | 2.1 |

Formulation B

Spray dried tiotropium bromide:leucine 75:25 wt % (4.2 mg) was added into a coated (DuPont 3200 200) canister, with Bespak 63 µl valve. HFA 227 with 0.1% w/w Abs Ethanol (14200 mg) was added to the canister. The suspension was shaken.
Anderson Cascade Impactor

| | |
|---|---|
| Delivered Dose (µg) | 13.5 |
| FPD (µg) | 6.8 |
| FPF (%) | 49.9 |
| MMAD (µm) | 2.5 |
| GSD | 1.9 |

Example 6

Formulation 4 (Tiotropium Bromide:Leucine 85:15 Wt %)

Tiotropium bromide (1.9 g) and L-leucine (0.3 g) were dissolved into 60 ml methanol. Water (60 ml) was added and shaken until dissolution occurred. The resultant solution was spray dried according to the parameters outlined below.
Bulk Particle Size Data—Sympatec Data

TABLE 6

| | Formulation 4 | | | |
|---|---|---|---|---|
| | X10 (µm) | X50 (µm) | X90 (µm) | X99 (µm) |
| 0 days | 0.61 | 1.25 | 2.32 | 3.77 |
| 9 days | 0.57 | 1.22 | 2.31 | 3.96 |
| 14 days | 0.55 | 1.20 | 2.29 | 3.93 |

Bulk DSC Data
T=0 days Tg=79° C., no other events
T=9 days Tg=65° C., small re-crystallisation followed by melting with decomposition above 200° C.
T=14 days Tg=62° C., broad re-crystallisation followed by melting with decomposition above 200° C.
T=35 days Tg=69° C., melting with decomposition above 200° C.

Formulation A

Spray dried tiotropium bromide:leucine 85:15 wt % (3.7 mg) was added into a coated (DuPont 3200 200) canister, with Bespak 63 µl valve. HFA 227 (14300 mg) was added to the canister. The solution was shaken.
Anderson Cascade Impactor

| | |
|---|---|
| Delivered Dose (µg) | 13.5 |
| FPD (µg) | 7.7 |
| FPF (%) | 57.5 |
| MMAD (µm) | 2.9 |
| GSD | 1.9 |

Formulation B

Spray dried tiotropium bromide:leucine 85:15 wt % (3.7 mg) was added into a coated (DuPont 3200 200) canister, with Bespak 63 µl valve. HFA 227 with 0.1% w/w Abs Ethanol (14200 mg) was added to the canister. The suspension was shaken.
Anderson Cascade Impactor

| | |
|---|---|
| Delivered Dose (µg) | 10.8 |
| FPD (µg) | 6.4 |
| FPF (%) | 58.8 |
| MMAD (µm) | 2.7 |
| GSD | 2.0 |

Extra Budesonide Examples

All samples have a clear glass transition at each time point, demonstrating that the spray dried formulations are amorphous. For all samples except Formulation 2 above there is a decrease in the $T_g$ during the storage time. All glass transition temperatures ($T_g$) are above 50° C. indicating that the samples are stable at room temperature.

Example 7

Formulation 5 (Budesonide:Trehalose 50:50)

Recrystallisation at 103° C. and large melt at 254° C. at 13 days indicates budesonide is, at least in part, amorphous but has become able to recrystallise on heating.

Example 8

Formulation 6 (Budesonide:Trehalose 75:25)

Budesonide remains amorphous at 13 days, but is more readily crystallised than at t=0.

Example 9

Formulation 7 (Budesonide:Trehalose:Leucine 50:25:25)

Large melt indicates that budesonide is mostly crystalline.

Example 10

Formulation 8 (Tiotropium Bromide:Trehalose 75:25)

Large recrystallisation at 98° C. with melting point of 186° C. at 13 days indicates that the formulation remains amorphous but is more readily crystallised than at t=0 days.

Example 11

Formulation 9 (Tiotropium Bromide:Trehalose:Leucine 50:25:25)

No indication of re-crystallisation, No information can be drawn from the t=13 day trace.

From the above Examples, one can see that the spray dried tiotropium bromide formulations produced have been shown to be amorphous at the time of manufacture and after storage at room temperature for 14 days.

It was also shown that tiotropium:leucine combinations (i.e. no trehalose) sediment quickly (<10 seconds) and therefore are poor suspension formulations.

FTIR data from the formulation comprising 50:25:25 Tiotropium Bromide:Trehalose:Leucine in HFA 134a shows that the formulation is at least substantially crystalline, which suggests that HFA 227 is preferred over HFA 134a.

Example 12

Spray Dried Tiotropium Bromide

Tiotropium bromide (1.0 g) was dissolved in water (200 ml). The resultant solution was spray dried according to the parameters outlined above.

Bulk Particle Size Data—Sympatec Data

TABLE 7

|  | X10 (μm) | X50 (μm) | X90 (μm) | X99 (μm) |
|---|---|---|---|---|
| 0 days | 0.5 | 1.1 | 2.1 | 27.3 |
| 14 days | 0.6 | 1.3 | 5.0 | 38.3 |

Bulk DSC Data

T=0 days Tg=64° C., no other events
T=14 days Tg=53° C., no other events

FTIR

No change over 14 days.

Formulation A

Spray dried tiotropium bromide (4.3 mg) was added into a coated (DuPont 3200 200) canister, with Bespak 50 μl valve. HFA 227 (17000 mg) was added to the canister. The solution was shaken.

| Anderson Cascade Impactor | | |
|---|---|---|
|  | 0 week | 7 weeks |
| Delivered Dose (μg) | 16.7 | 18.0 |
| FPD (μg) | 1.5 | 0.9 |
| FPF (%) | 9.0 | 4.8 |
| MMAD (μm) | 9.8 | 9.9 |
| GSD | 2.8 | 2.0 |

Formulation B

Spray dried tiotropium bromide (4.3 mg) was added into a coated (DuPont 3200 200) canister, with Bespak 50 μl valve. HFA 134a (14300 mg) was added to the canister. The solution was shaken.

| Anderson Cascade Impactor | | |
|---|---|---|
|  | 0 week | 7 weeks |
| Delivered Dose (μg) | 18.9 | 22.7 |
| FPD (μg) | 3.0 | 0.4 |
| FPF (%) | 10.5 | 1.9 |
| MMAD (μm) | 8.2 | 11.3 |
| GSD | 2.6 | 2.0 |

Example 13

Spray Dried Tiotropium Bromide:PVP 95:5 Wt %

Tiotropium bromide (0.95 g) and PVP (0.05 g) were dissolved into 50 ml water. The resultant solution was spray dried according to the parameters outlined below Bulk Particle Size Data—Sympatec Data

TABLE 8

|  | X10 (μm) | X50 (μm) | X90 (μm) | X99 (μm) |
|---|---|---|---|---|
| 0 days | 0.5 | 1.1 | 2.2 | 3.6 |
| 14 days | 0.5 | 1.2 | 2.4 | 4.2 |

Bulk DSC Data

T=0 days Tg=65° C., no other events
T=14 days Tg=51° C., no other events

FTIR

No change over 14 days.

Formulation A

Spray dried tiotropium bromide:PVP 95:5 wt % (4.5 mg) was added into a coated (DuPont 3200 200) canister, with Bespak 50 μl valve. HFA 227 (17000 mg) was added to the canister. The solution was shaken.

| Anderson Cascade Impactor | | |
| --- | --- | --- |
| | 0 week | 7 weeks |
| Delivered Dose (μg) | 20.6 | 21.0 |
| FPD (μg) | 2.2 | 4.1 |
| FPF (%) | 10.6 | 19.3 |
| MMAD (μm) | 7.3 | 5.0 |
| GSD | 2.8 | 3.2 |

Formulation B

Spray dried tiotropium bromide:PVP 95:5 wt % (4.5 mg) was added into a coated (DuPont 3200 200) canister, with Bespak 50 μl valve. HFA 227 & 0.1% Ethanol (17000 mg) was added to the canister. The solution was shaken.

| Anderson Cascade Impactor | | |
| --- | --- | --- |
| | 0 week | 7 weeks |
| Delivered Dose (μg) | 17.6 | 17.0 |
| FPD (μg) | 1.8 | 3.6 |
| FPF (%) | 10.4 | 21.2 |
| MMAD (μm) | 7.5 | 4.9 |
| GSD | 2.9 | 3.9 |

Example 14

Spray Dried Tiotropium Bromide:PVP 90:10 Wt %

Tiotropium bromide (0.90 g) and PVP (0.09 g) were dissolved into 50 ml water. The resultant solution was spray dried according to the parameters outlined below Bulk Particle Size Data—Sympatec Data

TABLE 9

| | X10 (μm) | X50 (μm) | X90 (μm) | X99 (μm) |
| --- | --- | --- | --- | --- |
| 0 days | 0.5 | 1.3 | 2.8 | 4.2 |

Bulk DSC Data
T=0 days Tg=53° C., no other events
T=14 days Tg=54° C., no other events
FTIR
No change over 14 days.
Formulation A Spray dried tiotropium bromide:PVP 90:10 wt % (4.8 mg) was added into a coated (DuPont 3200 200) canister, with Bespak 50 μl valve. HFA 227 (17000 mg) was added to the canister. The solution was shaken.

| Anderson Cascade Impactor | | |
| --- | --- | --- |
| | 0 week | 7 weeks |
| Delivered Dose (μg) | 16.4 | 18.3 |
| FPD (μg) | 2.4 | 5.7 |
| FPF (%) | 14.9 | 31.0 |
| MMAD (μm) | 5.3 | 3.4 |
| GSD | 2.1 | 2.9 |

Formulation B

Spray dried tiotropium bromide:PVP 90:10 wt % (4.8 mg) was added into a coated (DuPont 3200 200) canister, with Bespak 50 μl valve. HFA 227 & 0.1% Ethanol (17000 mg) was added to the canister. The solution was shaken.

| Anderson Cascade Impactor | | |
| --- | --- | --- |
| | 0 week | 7 weeks |
| Delivered Dose (μg) | 16.2 | 15.7 |
| FPD (μg) | 2.4 | 4.4 |
| FPF (%) | 14.9 | 28.3 |
| MMAD (μm) | 5.5 | 3.7 |
| GSD | 2.6 | 2.9 |

Example 15

Spray Dried Tiotropium Bromide:Lecithin 95:5 Wt %

Tiotropium bromide (0.95 g) and lecithin (0.05 g) were dissolved into methanol (30 ml). The solutions were combined by shaking. Water (20 ml) was added and shaken until dissolution occurred. The resultant solution was spray dried according to the parameters outlined above.

Bulk Particle Size Data—Sympatec Data

TABLE 10

| | X10 (μm) | X50 (μm) | X90 (μm) | X99 (μm) |
| --- | --- | --- | --- | --- |
| 0 days | 0.8 | 2.1 | 5.5 | 9.1 |
| 14 days | 1.0 | 3.1 | 29.8 | 48.6 |

Bulk DSC Data
T=0 days Tg=56° C., no other events
T=14 days Tg=53° C.
FTIR
No change over 14 days.
Formulation A Spray dried tiotropium bromide/lecithin 95:5 wt % (4.5 mg) was added into a coated (DuPont 3200 200) canister, with Bespak 500 valve. HFA 227 (17000 mg) was added to the canister. The solution was shaken.

| Anderson Cascade Impactor | |
| --- | --- |
| | 0 Week |
| Delivered Dose (μg) | 28 |
| FPD (μg) | 1.6 |
| FPF (%) | 5.8 |
| MMAD (μm) | 12.5 |
| GSD | 2.2 |

Formulation B

Spray dried tiotropium bromide/Lecithin 95:5 wt % (4.5 mg) was added into a coated (DuPont 3200 200) canister, with Bespak 50 μl valve. HFA 134a (14300 mg) was added to the canister. The solution was shaken.

| Anderson Cascade Impactor | |
| --- | --- |
| | 0 Week |
| Delivered Dose (μg) | 69.2 |
| FPD (μg) | 2.1 |
| FPF (%) | 3.0 |
| MMAD (μm) | 14.7 |
| GSD | 1.7 |

Example 16

Spray Dried Tiotropium Bromide:Lecithin 90:10 Wt %

Tiotropium bromide (0.90 g) and lecithin (0.09 g) were dissolved into methanol (30 ml). The solutions were combined by shaking. Water (20 ml) was added and shaken until dissolution occurred. The resultant solution was spray dried according to the parameters outlined above.

Bulk Particle Size Data—Sympatec Data

TABLE 11

|  | X10 (μm) | X50 (μm) | X90 (μm) | X99 (μm) |
| --- | --- | --- | --- | --- |
| 0 days | 1.0 | 3.5 | 32.7 | 57.2 |

Bulk DSC Data
T=0 days Tg=54° C., no other events
T=14 days Tg=50° C.
FTIR
No change over 14 days.
Formulation A
Spray dried tiotropium bromide:lecithin 90:10 wt % (4.8 mg) was added into a coated (DuPont 3200 200) canister, with Bespak 50 μl valve. HFA 227 (17000 mg) was added to the canister. The solution was shaken.

| Anderson Cascade Impactor | |
| --- | --- |
|  | 0 Week |
| Delivered Dose (μg) | 27.2 |
| FPD (μg) | 1.3 |
| FPF (%) | 4.7 |
| MMAD (μm) | 14.7 |
| GSD | 2.0 |

Formulation B
Spray dried tiotropium bromide:lecithin 90:10 wt % (4.8 mg) was added into a coated (DuPont 3200 200) canister, with Bespak 50 μl valve. HFA 134a (14300 mg) was added to the canister. The solution was shaken.

| Anderson Cascade Impactor | |
| --- | --- |
|  | 0 Week |
| Delivered Dose (μg) | 27.5 |
| FPD (μg) | 1.5 |
| FPF (%) | 5.4 |
| MMAD (μm) | 12.2 |
| GSD | 2.0 |

Salbutamol Sulphate/Ipratropium Bromide Spray Dried Examples:

Formulations containing salbutamol sulphate, ipratropium bromide, trehalose and leucine were prepared by spray drying using a Mini spray dryer.

The spray dried powders were characterised by particle size using a Sympatec laser sizer, infra-red spectroscopy using a Perkin Elmer Spectrum GX ATR-FTIR, and thermal behaviour using a Perkin Elmer Diamond differential scanning calorimeter.

Samples of each formulation (250 mg) were stored at room temperature and low RH (20-30%) in glass 7 mL screw top vials and the characterisation repeated after 7 and 14 days.

Differential Scanning calorimetry
The sample (5 to 10 mg) was sealed in a pierced 40 μl aluminium sample pan and heated from 20 to 200° C. at 50° C. per minute.

There are no significant changes in the particle size distributions for any of the formulations over fourteen days.

Example 17

Salbutamol:Ipratropium Bromide 85.7:14.3 Wt % (100% Api)

|  | X10 (μm) | X50 (μm) | X90 (μm) | X99 (μm) |
| --- | --- | --- | --- | --- |
| 0 days | 0.48 | 1.17 | 2.45 | 4.14 |
| 7 days | 0.45 | 1.15 | 2.47 | 4.11 |
| 14 days | 0.47 | 1.17 | 2.47 | 4.13 |

T=0 days Tg=71° C., broad re-crystallisation 110 to 160° C. followed by melting with decomposition above 160° C.
T=7 days Tg=64° C., broad re-crystallisation 110 to 170° C. followed by melting with decomposition above 180° C.
T=14 days Tg=70° C., broad re-crystallisation 110 to 170° C. followed by melting with decomposition above 170° C.
pMDI Manufacture: Spray dried salbutamol sulphate:ipratropium bromide (22.5 mg) was added into a coated (DuPont 3200 200) canister, with Bespak 63 μl valve. HFA 227 (17000 mg) was added to the canister. The solution was shaken.

Example 18

Salbutamol:Ipratropium Bromide:Trehalose:Leucine 77.1:12.9:5:5%

|  | X10 (μm) | X50 (μm) | X90 (μm) | X99 (μm) |
| --- | --- | --- | --- | --- |
| 0 days | 0.51 | 1.18 | 2.30 | 3.78 |
| 7 days | 0.54 | 1.20 | 2.32 | 3.86 |
| 14 days | 0.55 | 1.23 | 2.39 | 3.88 |

T=0 days Tg=67° C., broad re-crystallisation 110 to 160° C. followed by melting with decomposition above 160° C.
T=7 days Tg=60° C., broad re-crystallisation 110 to 160° C. followed by melting with decomposition above 180° C.
T=14 days Tg=64° C., broad re-crystallisation 110 to 170° C. followed by melting with decomposition above 170° C.
pMDI Manufacture: Spray dried salbutamol sulphate:ipratropium bromide:Trehalose:Leucine 77.1:12.9:5:5 wt % (25.0 mg) was added into a coated (DuPont 3200 200) canister, with Bespak 63 μl valve. HFA 227 (17000 mg) was added to the canister. The solution was shaken.

Example 19

Salbutamol:Ipratropium Bromide:Trehalose:Leucine 68.6:11.4:10:10 Wt %

|  | X10 (μm) | X50 (μm) | X90 (μm) | X99 (μm) |
| --- | --- | --- | --- | --- |
| 0 days | 0.65 | 1.34 | 2.50 | 3.73 |
| 7 days | 0.58 | 1.28 | 2.46 | 3.72 |
| 14 days | 0.64 | 1.36 | 2.58 | 3.81 |

T=0 days Tg=81° C., broad re-crystallisation 110 to 170° C. followed by melting with decomposition above 180° C.
T=7 days Tg=44° C., possibly two broad re-crystallisation events followed by melting with decomposition above 180° C.
T=14 days Tg=72° C., large broad re-crystallisation 110 to 160° C. followed by melting with decomposition above 160° C.

pMDI Manufacture: Spray dried salbutamol sulphate:ipratropium bromide:Trehalose:Leucine 68.6:11.4:10:10 wt % (28.1 mg) was added into a coated (DuPont 3200 200) canister, with Bespak 63 µl valve. HFA 227 (17000 mg) was added to the canister. The solution was shaken.

Example 20

Salbutamol:Ipratropium Bromide:Trehalose:Leucine 60:10:15:15 Wt %

|  | X10 (µm) | X50 (µm) | X90 (µm) | X99 (µm) |
| --- | --- | --- | --- | --- |
| 0 days | 0.65 | 1.40 | 2.72 | 4.05 |
| 7 days | 0.62 | 1.37 | 2.65 | 3.98 |
| 14 days | 0.68 | 1.44 | 2.79 | 4.19 |

T=0 days Tg=76° C., re-crystallisation around 120° C. followed by melting with decomposition above 180° C.
T=7 days Tg=66° C., re-crystallisation around 110° C. followed by melting with decomposition above 180° C.
T=14 days Tg=74° C., re-crystallisation around 125° C. followed by melting with decomposition above 180° C.

pMDI Manufacture: Spray dried salbutamol sulphate:ipratropium bromide:Trehalose:Leucine 60:10:15:15 wt % (32.1 mg) was added into a coated (DuPont 3200 200) canister, with Bespak 63 µl valve. HFA 227 (17000 mg) was added to the canister. The solution was shaken.

All samples have a clear glass transition at each time point, demonstrating that the spray dried formulations are amorphous. All glass transition temperatures (Tg) remain well above room temperature. For all samples there is a decrease in the Tg after 7 days which is partly recovered at 14 days. This is most apparent for the batch in Example 19. The reason for this change would have to be investigated further to be substantiated.

Infra-Red Spectroscopy

The absorbance spectra were measured using the Golden Gate attenuated total reflectance (ATR) accessory between 4000 and 600 cm$^{-1}$ acquiring 16 co-added scans. The spectra were compared with that of the crystalline staring materials and between time points.

Spectra recorded at 7 and 14 days showed broad, undefined peaks in the fingerprint regions and lack of any sharp peaks above 3000 cm$^{-1}$ indicating that the samples are amorphous. The spectra showed only minor differences between batches, demonstrating that the spectra are dominated by absorbances due to salbutamol and ipratropium.

Conclusions

The spray dried formulations produced have been shown to be amorphous at the time of manufacture and after storage at room temperature and low humidity for 14 days.

pMDI Manufacture:

Example 21

Spray dried salbutamol sulphate/ipratropium bromide (22.5 mg) as per Example 17 was added into a coated (DuPont 3200 200) canister, with Bespak 63 µl valve. 0.1% Ethanol, HFA 227 (17000 mg) was added to the canister. The solution was shaken.

Example 22

Spray dried salbutamol sulphate/ipratropium bromide:Trehalose:Leucine 77.1:12.9:5:5 wt % (25.0 mg) as per Example 18 was added into a coated (DuPont 3200 200) canister, with Bespak 63 µl valve. 0.1% Ethanol, HFA 227 (17000 mg) was added to the canister. The solution was shaken.

Example 23

Spray dried salbutamol sulphate/ipratropium bromide:Trehalose:Leucine 68.6:11.4:10:10 wt %. (28.1 mg) as per Example 19 was added into a coated (DuPont 3200 200) canister, with Bespak 63 ti valve. 0.1% Ethanol, HFA 227 (17000 mg) was added to the canister. The solution was shaken.

Example 24

Spray dried salbutamol sulphate/ipratropium bromide:Trehalose:Leucine 60:10:15:15 wt % (32.1 mg) as per Example 20 was added into a coated (DuPont 3200 200) canister, with Bespak 63 µl valve. 0.1% Ethanol, HFA 227 (17000 mg) was added to the canister. The solution was shaken.

TABLE 12

| Anderson Cascade Impactor Salbutamol Sulphate Summary | | | | | | | | | |
| --- | --- | --- | --- | --- | --- | --- | --- | --- | --- |
| Example | | | DD (µg) Weeks | | FPD (µg) Weeks | | FPF (%) Weeks | | MMAD (µm) Weeks |
| Number | Product/Blend | Formulation | 0 | 10 | 0 | 10 | 0 | 10 | 0 | 10 |
| 17 | 85.7:14.3:0:0 | HFA 227 | 81 | 79 | 35 | 30 | 43 | 38 | 3.6 | 3.7 |
| 18 | 77.1:12.9:5:5 | HFA 227 | 83 | 81 | 36 | 33 | 43 | 41 | 3.8 | 3.8 |
| 19 | 68.6:11.4:10:10 | HFA 227 | 73 | 69 | 42 | 32 | 58 | 46 | 3.3 | 3.7 |
| 20 | 60:10:15:15 | HFA 227 | 75 | 71 | 30 | 26 | 39 | 28 | 3.9 | 4.1 |
| 21 | 85.7:14.3:0:0 | 0.1% EtOH, 227 | 77 | 67 | 32 | 15 | 41 | 22 | 3.8 | 4.8 |
| 22 | 77.1:12.9:5:5 | 0.1% EtOH, 227 | 72 | 69 | 31 | 18 | 43 | 41 | 3.7 | 4.8 |
| 23 | 68.6:11.4:10:10 | 0.1% EtOH, 227 | 73 | 69 | 42 | 19 | 58 | 46 | 3.3 | 4.7 |
| 24 | 60:10:15:15 | 0.1% EtOH, 227 | 66 | 70 | 25 | 20 | 38 | 36 | 3.9 | 4.6 |

TABLE 13

Anderson Cascade Impactor Ipratropium Bromide Summary

| Example Number; | Product/Blend | Formulation | DD (μg) Weeks 0 | DD (μg) Weeks 10 | FPD (μg) Weeks 0 | FPD (μg) Weeks 10 | FPF (%) Weeks 0 | FPF (%) Weeks 10 | MMAD (μm) Weeks 0 | MMAD (μm) Weeks 10 |
|---|---|---|---|---|---|---|---|---|---|---|
| 17 | 85.7:14.3:0:0 | HFA 227 | 14 | 13 | 6.1 | 4.9 | 45 | 37 | 3.6 | 3.8 |
| 18 | 77.1:12.9:5:5 | HFA 227 | 12 | 13 | 6.1 | 5.5 | 50 | 42 | 3.6 | 3.8 |
| 19 | 68.6:11.4:10:10 | HFA 227 | 13 | 12 | 7.4 | 5.6 | 57 | 46 | 3.3 | 3.7 |
| 20 | 60:10:15:15 | HFA 227 | 12 | 11 | 4.7 | 3.8 | 39 | 35 | 3.7 | 4.2 |
| 21 | 85.7:14.3:0:0 | 0.1% EtOH, 227 | 13 | 11 | 5.3 | 2.2 | 40 | 20 | 3.8 | 5.2 |
| 22 | 77.1:12.9:5:5 | 0.1% EtOH, 227 | 13 | 12 | 5.7 | 3.1 | 45 | 26 | 3.6 | 4.8 |
| 23 | 68.6:11.4:10:10 | 0.1% EtOH, 227 | 12 | 11 | 5.6 | 3.1 | 48 | 27 | 3.7 | 4.7 |
| 24 | 60:10:15:15 | 0.1% EtOH, 227 | 11 | 11 | 3.9 | 3.0 | 37 | 26 | 4.0 | 4.8 |

(Formulations containing ethanol show a greater decrease in FPD than formulations without ethanol after 10 weeks storage. Metered and delivered dose remains consistent over 10 weeks.)

Spray Dried Salbutamol Sulphate with Alternative Excipients

Example 25

Spray Dried Salbutamol

| | X10 (μm) | X50 (μm) | X90 (μm) | X99 (μm) |
|---|---|---|---|---|
| 0 days | 0.5 | 1.4 | 3.2 | 5.0 |
| 14 days | 0.6 | 1.4 | 3.0 | 4.9 |

Bulk DSC Data
T=0 days Tg=81° C., no other events
T=14 days Tg=77° C.
FTIR
　No change over 14 days.
pMDI Manufacture:

Example 25A

Spray dried salbutamol sulphate (28.8 mg) was added into a coated (DuPont 3200 200) canister, with Bespak 63 μl valve. HFA 227 (17000 mg) was added to the canister. The solution was shaken.

Example 25B

Spray dried salbutamol sulphate (22.8 mg) was added into a coated (DuPont 3200 200) canister, with Bespak 63 μl valve. HFA 134a (14300 mg) was added to the canister. The solution was shaken.

Example 26

Spray Dried Salbutamol Sulphate:PVP (95:5 wt %)

| | X10 (μm) | X50 (μm) | X90 (μm) | X99 (μm) |
|---|---|---|---|---|
| 0 days | 0.5 | 1.2 | 2.5 | 5.0 |
| 14 days | 0.6 | 1.2 | 2.5 | 4.9 |

Bulk DSC Data
T=0 days Tg=77° C., no other events
T=14 days Tg=78° C.
FTIR
　No change over 14 days
pMDI Manufacture:

Example 26A

Spray dried salbutamol sulphate:PVP 95:5 wt % (30.3 mg) was added into a coated (DuPont 3200 200) canister, with Bespak 63 μl valve. HFA 227 (17000 mg) was added to the canister. The solution was shaken.

Example 26B

Spray dried salbutamol sulphate:PVP 95:5 wt % (30.3 mg) was added into a coated (DuPont 3200 200) canister, with Bespak 63 μA valve. 0.1% Ethanol in HFA 227 (17000 mg) was added to the canister. The solution was shaken.

Example 27

Spray Dried Salbutamol Sulphate:PVP (90:10 wt %)

| | X10 (μm) | X50 (μm) | X90 (μm) | X99 (μm) |
|---|---|---|---|---|
| 0 days | 0.5 | 1.4 | 3.4 | 5.2 |
| 14 days | 0.6 | 1.5 | 3.4 | 5.3 |

Bulk DSC Data
T=0 days Tg=59° C.
T=14 days Tg=84° C.
FTIR
　No change over 14 days.
pMDI Manufacture:

Example 27A

Spray dried salbutamol sulphate:PVP 90:10 wt % (32.0 mg) was added into a coated (DuPont 3200 200) canister, with Bespak 63 μl valve. HFA 227 (17000 mg) was added to the canister. The solution was shaken.

Example 27B

Spray dried salbutamol sulphate:PVP 90:10 wt % (32.0 mg) was added into a coated (DuPont 3200 200) canister, with Bespak 63 μl valve. 0.1% Ethanol in HFA 227 (17000 mg) was added to the canister. The solution was shaken.

Example 28

Spray Dried Salbutamol Sulphate:Lecithin (95:5 wt %)

|         | X10 (μm) | X50 (μm) | X90 (μm) | X99 (μm) |
|---------|----------|----------|----------|----------|
| 0 days  | 0.5      | 1.5      | 3.5      | 5.3      |
| 14 days | 0.6      | 1.5      | 3.5      | 5.3      |

Bulk DSC Data
T=0 days Tg=71° C., no other events
T=14 days Tg=76° C.

FTIR
No change over 14 days.
pMDI Manufacture:

Example 28A

Spray dried salbutamol sulphate:Lecithin 95:5 wt % (30.3 mg) was added into a coated (DuPont 3200 200) canister, with Bespak 63 μl valve. HFA 227 (17000 mg) was added to the canister. The solution was shaken.

Example 28B

Spray dried salbutamol sulphate:Lecithin 95:5 wt % (30.3 mg) was added into a coated (DuPont 3200 200) canister, with Bespak 63 μl valve. HFA 134a (14300 mg) was added to the canister. The solution was shaken.

Example 29

Spray Dried Salbutamol Sulphate:Lecithin (90:10 wt %)

|         | X10 (μm) | X50 (μm) | X90 (μm) | X99 (μm) |
|---------|----------|----------|----------|----------|
| 0 days  | 0.5      | 1.1      | 2.2      | 4.8      |
| 14 days | 0.6      | 1.2      | 2.2      | 4.6      |

Bulk DSC Data
T=0.0 days Tg=76° C., no other events
T=14 days Tg=77° C.
FTIR
No change over 14 days.

pMDI Manufacture:

Example 29A

Spray dried salbutamol sulphate:Lecithin 90:10 wt % (32.0 mg) was added into a coated (DuPont 3200 200) canister, with Bespak 63 μl valve. HFA 227 (17000 mg) was added to the canister. The solution was shaken.

Example 29B

Spray dried salbutamol sulphate:Lecithin 90:10 wt % (32.0 mg) was added into a coated (DuPont 3200 200) canister, with Bespak 63 μl valve. HFA 134a (14300 mg) was added to the canister. The solution was shaken.

TABLE 14

Summary data salbutamol sulphate with excipients

| Excipient    | Example | HFA            | DD (μg) | FPD (μg) | FPF (%) | MMAD | GSD |
|--------------|---------|----------------|---------|----------|---------|------|-----|
| None         | 25A     | 227            | 86      | 42       | 49      | 3.3  | 1.5 |
|              | 25B     | 134            | 99      | 47       | 48      | 3.4  | 1.6 |
| 5% PVP       | 26A     | 227            | 75      | 24       | 33      | 5.0  | 1.8 |
|              | 26B     | 0.1% EtOH, 227 | 78      | 37       | 48      | 3.3  | NA  |
| 10% PVP      | 27A     | 227            | 73      | 38       | 53      | 3.2  | 1.6 |
|              | 27B     | 0.1% EtOH, 227 | 85      | 39       | 46      | 3.4  | 1.6 |
| 5% Lecithin  | 28A     | 227            | 65      | 16       | 24      | 4.4  | NA  |
|              | 28B     | 134            | 66      | 15       | 23      | 4.6  | NA  |
| 10% Lecithin | 29A     | 227            | 88      | 18       | 21      | 5.1  | NA  |
|              | 29B     | 134            | 100     | 20       | 20      | 5.2  | NA  |

Spray Dried Blends (not Used in pMDI Formulations)

Example 30

Spray Dried Fomoterol Fumarate

|         | X10 (μm) | X50 (μm) | X90 (μm) | X99 (μm) |
|---------|----------|----------|----------|----------|
| 14 days | 0.9      | 1.9      | 3.6      | 5.7      |

Bulk DSC Data
T=0 days Tg=62° C., no other events
T=14 days Tg=74° C.
FTIR
No change over 14 days

Example 31

Spray Dried Fomoterol Fumarate:Leucine:Trehalose 80:10:10 wt %

|         | X10 (μm) | X50 (μm) | X90 (μm) | X99 (μm) |
|---------|----------|----------|----------|----------|
| 0 days  | 0.7      | 1.6      | 3.8      | 7.2      |
| 14 days | 0.8      | 1.5      | 3.5      | 6.8      |

Bulk DSC Data
T=0 days Tg=65° C., no other events
T=14 days Tg=65° C.
FTIR
No change over 14 days

Example 32

Spray Dried Budesonide

|  | X10 (μm) | X50 (μm) | X90 (μm) | X99 (μm) |
|---|---|---|---|---|
| 0 days | 0.8 | 2.0 | 6.0 | 70.3 |
| 14 days | 0.8 | 1.8 | 4.3 | 7.0 |

Bulk DSC Data
T=0 days Tg=82° C., no other events
T=14 days Tg=81° C.
FTIR
  No change over 14 days

Example 33

Spray Dried Budesonide:Trehalose:Leucine 80:10:10 wt %

|  | X10 (μm) | X50 (μm) | X90 (μm) | X99 (μm) |
|---|---|---|---|---|
| 0 days | 0.9 | 1.9 | 3.8 | 6.3 |
| 14 days | 0.9 | 1.9 | 3.7 | 5.9 |

Bulk DSC Data
T=0 days Tg=82° C., no other events
T=14 days Tg=81° C.
FTIR
  No change over 14 days

Example 34

Spray Dried Budesonide & Fomoterol Fumarate:Trehalose:Leucine 80 (Budesonide & Fomoterol Fumarate):10:10 wt %

|  | X10 (μm) | X50 (μm) | X90 (μm) | X99 (μm) |
|---|---|---|---|---|
| 0 days | 0.8 | 1.7 | 3.6 | 6.3 |
| 14 days | 0.8 | 1.7 | 3.4 | 5.6 |

Bulk DSC Data
T=0 days Tg=75° C., no other events
T=14 days Tg=79° C.
FTIR
  No change over 14 days

The invention claimed is:

1. A suspension formulation comprising:
   particles comprising a pharmaceutically active agent, wherein the pharmaceutically active agent is tiotropium;
   a propellant; and
   trehalose and leucine as suspension stabilisers, wherein the composition comprises an amount of trehalose of 0.0003 to 0.02% by weight of the formulation.

2. A suspension formulation as claimed in claim 1, wherein the trehalose and/or leucine are coated on the particles comprising the pharmaceutically active agent.

3. A suspension formulation as claimed in claim 1, wherein the trehalose and/or leucine are incorporated into the particles comprising the pharmaceutically active agent.

4. A suspension formulation as claimed in claim 1, wherein the suspension stabilisers allow the pharmaceutically active agent to retain its physical state.

5. A suspension formulation as claimed in claim 4, wherein an amorphous state of the pharmaceutically active agent is retained.

6. A suspension formulation as claimed in claim 1, further comprising a co-solvent in an amount which does not substantially enhance the solubility of the pharmaceutically active agent in the formulation.

7. A suspension formulation as claimed in claim 6, wherein the co-solvent is ethanol.

8. A suspension formulation as claimed in claim 7, wherein the ethanol is present in an amount of less than 1% w/w based upon the total formulation.

9. A suspension formulation as claimed in claim 1, wherein the particles comprising the pharmaceutically active agent are formed by spray drying.

10. A suspension formulation as claimed in claim 9, wherein the particles comprising the pharmaceutically active agent are formed by co-spray drying the pharmaceutically active agent and the suspension stablisers.

11. A suspension formulation as claimed in claim 1, wherein the propellant comprises HFA 227, HFA 134a or a combination thereof.

12. A suspension formulation as claimed in claim 1, further comprising one or more of surfactants, lubricants, flavouring agents and additives.

13. A suspension formulation according to claim 1 further comprising a vinyl polymer.

14. A suspension formulation according to claim 13, wherein the vinyl polymer is polyvinylpyrrolidone.

15. A method for preparing a suspension formulation as claimed in claim 1, wherein the method includes forming the particles comprising the pharmaceutically active agent by spray drying and adding the spray dried particles to the propellant.

16. A method as claimed in claim 15, wherein the pharmaceutically active agent is co-spray dried with the suspension stabilisers.

17. A method as claimed in claim 15, wherein the suspension stabilisers are coated on surfaces of the spray dried particles comprising the pharmaceutically active agent by milling.

* * * * *